(12) United States Patent
Valentino et al.

(10) Patent No.: US 9,115,989 B2
(45) Date of Patent: Aug. 25, 2015

(54) SYSTEM FOR MOTION AND ACTIVITY CORRELATION WITH DOSE FOR OCCUPATIONAL AND ENVIRONMENTAL DOSIMETRY

(71) Applicant: LANDAUER, INC., Glenwood, IL (US)

(72) Inventors: Daniel J. Valentino, Napersville, IL (US); R. Craig Yoder, Crown Point, IN (US)

(73) Assignee: LANDAUER, INC., Glenwood, IL (US)

( * ) Notice: Subject to any disclaimer, the term of this patent is extended or adjusted under 35 U.S.C. 154(b) by 0 days.

(21) Appl. No.: 14/551,176

(22) Filed: Nov. 24, 2014

(65) Prior Publication Data

US 2015/0081247 A1 Mar. 19, 2015

Related U.S. Application Data

(60) Division of application No. 14/289,349, filed on May 28, 2014, which is a continuation-in-part of application No. 14/274,082, filed on May 9, 2014, which is a continuation of application No. 13/906,553, (Continued)

(51) Int. Cl.
*G01J 1/00* (2006.01)
*G01C 19/00* (2013.01)
(Continued)

(52) U.S. Cl.
CPC .............. *G01C 19/00* (2013.01); *A61B 5/0022* (2013.01); *A61B 5/1112* (2013.01);
(Continued)

(58) Field of Classification Search
CPC .............. G01T 1/02; G01T 1/026; G01T 7/00

USPC ........................................................ 250/336.1
See application file for complete search history.

(56) References Cited

U.S. PATENT DOCUMENTS

| 3,646,347 A | 2/1972 | Farmer et al. |
| 5,731,590 A | 3/1998 | Miller |

(Continued)

FOREIGN PATENT DOCUMENTS

| EP | 2 378 581 A1 | 10/2011 |
| JP | 2007205766 A | 8/2007 |

(Continued)

OTHER PUBLICATIONS

S. R. Anton, H. A. Sodano, A review of power harvesting using piezo-electric materials (2003-2006), Smart Mater. and Struct. 16 (3) (2007) R1-R21. doi: 10.1088/0964-1726/16/3/R01.

(Continued)

*Primary Examiner* — Kiho Kim
(74) *Attorney, Agent, or Firm* — Alchemy-Partners, PC

(57) ABSTRACT

Described are a method and apparatus for determining based on motion data when an individual wearing a dosimeter is active. Also described are a method and apparatus for determining based on motion data whether an individual was wearing a dosimeter when the dosimeter was exposed to radiation. Also described are a method and apparatus for determining based on motion data whether a dosimeter was in a particular location when the dosimeter was exposed to radiation. Also described are a method and apparatus for determining based on motion data where on the body of an individual the individual was wearing a dosimeter when the dosimeter was exposed to radiation. Also described are a method and apparatus for determining based on motion data the probability that an individual is wearing a dosimeter that is assigned to the individual.

3 Claims, 15 Drawing Sheets

Related U.S. Application Data filed on May 31, 2013, now Pat. No. 8,822,924.

(60) Provisional application No. 61/654,162, filed on Jun. 1, 2012, provisional application No. 61/821,683, filed on May 9, 2013.

(51) Int. Cl.

| | |
|---|---|
| *G01P 13/00* | (2006.01) |
| *G01J 1/02* | (2006.01) |
| *G01J 1/42* | (2006.01) |
| *G01J 1/04* | (2006.01) |
| *G01T 1/02* | (2006.01) |
| *G01T 7/00* | (2006.01) |
| *G01P 15/14* | (2013.01) |
| *A61B 5/00* | (2006.01) |
| *G01P 15/00* | (2006.01) |
| *A61B 5/11* | (2006.01) |

(52) U.S. Cl.
CPC ............ *A61B 5/6898* (2013.01); *G01J 1/0219* (2013.01); *G01J 1/0488* (2013.01); *G01J 1/4204* (2013.01); *G01J 1/4228* (2013.01); *G01P 13/00* (2013.01); *G01P 15/14* (2013.01); *G01T 1/02* (2013.01); *G01T 1/026* (2013.01); *G01T 7/00* (2013.01); *A61B 5/1123* (2013.01); *G01P 15/00* (2013.01)

(56) References Cited

U.S. PATENT DOCUMENTS

| | | | |
|---|---|---|---|
| 6,127,685 | A | 10/2000 | Yoder et al. |
| 6,198,108 | B1 | 3/2001 | Schweitzer et al. |
| 6,846,434 | B2 | 1/2005 | Akselrod |
| 7,098,470 | B2 | 8/2006 | Akselrod |
| 7,777,396 | B2 | 8/2010 | Rastegar et al. |
| 7,898,096 | B1 | 3/2011 | Krupenkin |
| 7,964,851 | B2 | 6/2011 | Fehrenbacher |
| 8,674,526 | B2 | 3/2014 | Lemieux |
| 8,692,206 | B2 | 4/2014 | Hyde et al. |
| 8,704,387 | B2 | 4/2014 | Lemieux |
| 8,822,924 | B2 | 9/2014 | Valentino et al. |
| 2003/0031298 | A1 | 2/2003 | Xing |
| 2006/0185434 | A1* | 8/2006 | Bernhagen ...................... 73/649 |
| 2008/0217551 | A1 | 9/2008 | Zhang et al. |
| 2009/0010390 | A1 | 1/2009 | Saoudi et al. |
| 2009/0020703 | A1 | 1/2009 | Buckley et al. |
| 2009/0080138 | A1 | 3/2009 | Lohndorf et al. |
| 2010/0219494 | A1 | 9/2010 | Barnaby |
| 2012/0041685 | A1 | 2/2012 | Ding et al. |
| 2012/0132806 | A1 | 5/2012 | Findlay et al. |
| 2012/0181901 | A1 | 7/2012 | Krupenkin et al. |
| 2012/0238795 | A1* | 9/2012 | Bert et al. .......................... 600/1 |
| 2012/0319404 | A1 | 12/2012 | Joseph et al. |
| 2013/0312806 | A1 | 11/2013 | Carroll |

FOREIGN PATENT DOCUMENTS

| | | |
|---|---|---|
| KR | 1020040019525 A | 3/2004 |
| WO | 2008/109153 A1 | 9/2008 |
| WO | 2013/066882 A1 | 5/2013 |

OTHER PUBLICATIONS

S. P. Beeby, M. J. Tudor, N. M. White, Energy harvesting vibration sources for microsystems applications, Meas. Sci. and Tech. 17 (12) (2006) R175-R195. doi:10.1088/0957-0233/17/12/R01.

P. Mitcheson, E. Yeatman, G. Rao, A. Holmes, T. Green, Energy Harvesting From Human and Machine Motion for Wireless Electronic Devices, Proceedings of the IEEE 96 (9) (2008) 1457-1486. doi:10.1109/JPROC.2008.927494.

S. Roundy, P. K. Wright, A piezoelectric vibration based generator for wireless electronics, Smart Mater. and Struct. 13 (5) (2004) 1131-1142.

A. Erturk, D. J. Inman, An experimentally validated bimorph cantilever model for piezoelectric energy harvesting from base excitations, Smart Materials and Structures 18 (2) (2009) 025009.

D. F. Berdy, P. Srisungsitthisunti, B. Jung, X. Xu, J. F. Rhoads, D. Peroulis, Low-frequency meandering piezoelectric vibration energy harvester., IEEE transactions on ultrasonics, ferroelectrics, and frequency control 59 (5) (2012) 846-58. doi:10.1109/TUFFC.2012.2269.

C. Williams, R. Yates, Analysis of a micro-electric generator for microsystems, Proceedings of the International Solid-State Sensors and Actuators Conference—TRANSDUCERS '95 44 (0) (1995) 369-372. doi:10.1109/SENSOR.1995.717207.

S. P. Beeby, R. N. Torah, M. J. Tudor, P. Glynne-Jones, T. O'Donnell, C. R. Saha, S. Roy, A micro-electromagnetic generator for vibration energy harvesting, J. Micromech. Microeng. 17 (7) (2007) 1257-1265.

S. Roundy, P. Wright, J. Rabaey, A study of low level vibrations as a power source for wireless sensor nodes, Computer Communications 26 (2003) 1131-1144.

S. Meninger, J. Mur-Miranda, R. Amirtharajah, A. Chandrakasan, J. Lang, Vibration-to-electric energy conversion, IEEE Transactions on Very Large Scale Integration (VLSI) Systems 9 (1) (2001) 64-76.

L. Wang, F. G. Yuan, Vibration energy harvesting by magnetostrictive material, Smart Materials and Structures 17 (4) (2008) 045009.

E. K. Reilly, L. M. Miller, R. Fain, P. K. Wright, A study of ambient vibrations for piezoelectric energy conversion, in: Proc. PowerMEMS, Washington D.C., 2009, pp. 312-315.

S. Lam Po Tang, Recent developments in flexible wearable electronics for monitoring applications, Transactions of the Institute of Measurement and Control 29 (3-4) (2007) 283-300. doi:10.1177/0142331207070389.

B. Lo, S. Thiemjarus, R. King, G. Yang, Body sensor network: a wireless sensor platform for pervasive healthcare monitoring, Conference on Pervasive Computing Technologies for Healthcare (2005) 77-80.

K. Sun, G. Q. Liu, X. Y. Xu, Nonlinear Resonant Generator for Harvesting Energy from Human Wrist Vertical Shaking, Applied Mechanics and Materials 128-129 (2011) 923-927. doi:10.4028/www.scientific.net/AMM.128-129.923.

C. Saha, T. ODonnell, N. Wang, P. McCloskey, Electromagnetic generator for harvesting energy from human motion, Sensors and Actuators A: Physical 147 (1) (2008) 248-253. doi:10.1016/j.sna.2008.03.008.

P. Constantinou, P. H. Mellor, P. D. Wilcox, A Magnetically Sprung Generator for Energy Harvesting Applications, IEEE/ASME Transactions on Mechatronics 17 (3) (2012) 415-424. doi:10.1109/TMECH.2012.2188834.

X. Yang, B. Zhang, J. Li, Y. Wang, Model and Experimental Research on an Electromagnetic Vibration-Powered Generator With Annular Permanent Magnet Spring, IEEE Transactions on Applied Superconductivity 22 (3) (2012) 5201504-5201504. doi:10.1109/TASC.2011.2179401.

A. R. M. Foisal, B.-C. Lee, G.-S. Chung, Fabrication and performance optimization of an AA size electromagnetic energy harvester using magnetic spring, 2011 IEEE SENSORS Proceedings (2011) 1125-1128doi:10.1109/ICSENS.2011.6126947.

P. Constantinou, P. Mellor, P. Wilcox, A Model of a Magnetically Sprung Vibration Generator for Power Harvesting Applications, in: 2007 IEEE International Electric Machines & Drives Conference, IEEE, 2007, pp. 725-730. doi:10.1109/IEMDC.2007.382757.

E. Dallago, M. Marchesi, G. Venchi, Analytical Model of a Vibrating Electromagnetic Harvester Considering Nonlinear Effects, IEEE Transactions on Power Electronics 25 (8) (2010) 1989-1997. doi:10.1109/TPEL.2010.2044893.

B. Mann, N. Sims, Energy harvesting from the nonlinear oscillations of magnetic levitation, Journal of Sound and Vibration 319 (1-2) (2009) 515-530. doi:10.1016/j.jsv.2008.06.011.

(56) References Cited

OTHER PUBLICATIONS

A. R. M. Foisal, C. Hong, G.-S. Chung, Multi-frequency electromagnetic energy harvester using a magnetic spring cantilever, Sensors and Actuators A: Physical 182 (2012) 106-113. doi:10.1016/j.sna.2012.05.009.

G. P. Beyer, G. G. Mann, J. A. Pursley, E. T. Espenhahn, C. Fraisse, D. J. Godfrey, M. Oldham, T. B. Carrea, N. Bolick, and C. W. Scarantino, "An implantable MOSFET dosimeter for the measurement of radiation dose in tissue during cancer therapy," IEEE Sensors Journal, vol. 8, 2008.

Lars Botter-Jensen et al., Optically Stimulated Luminescence Dosimetry, Elesevier, 2003.

Akslerod, M. S., Kortov, V. S., and Gorelova, E. A., "Preparation and properties of Al2O3:C," Radiat. Prot. Dosim. 47, 159-164 (1993).

Akselrod, M. S., Lucas, A. C., Polf, J. C., McKeever, S. W. S., "Optically stimulated luminescence of Al2O3:C," Radiation Measurements, 29, (3-4), 391-399 (1998).

N. Stanford, Whole Body Dose Algorithm for the Landauer InLight Next Generation Dosimeter, Algorithm Revision: Next Gen IEC; Sep. 13, 2010.

N. Stanford, Whole Body Dose Algorithm for the Landauer InLight Next Generation Dosimeter, Algorithm Revision: Next Gen NVLAP; Sep. 27, 2010.

Ravi N, Dandekar N, Mysore P, Littman ML, "Activity Recognition from Accelerometer Data," American Association for Artificial Intelligence, 2005.

Casale P, Pujol O, Radeva P, "Human Activity Recognition from Accelerometer Data Using a Wearable Device," LNCS, 6669, 289-296, 2011.

Gafurov D, Helkala K, Sondrol T, "Biometric Gait Authentication Using Accelerometer Sensor," Journal of Computers, 1(7):51-59, 2006.

Bedogni L, Di Felice M, Bononi L, "By Train or By Car? Detecting the User's Motion Type through Smartphone Sensors Data," IEEE, 2012.

International Search Report dated Sep. 18, 2014 in corresponding International Application No. PCT/IB2014/061818.

International Search Report dated Sep. 18, 2014 in corresponding International Application No. PCT/IB2014/061819.

International Search Report dated Sep. 25, 2014 in corresponding International Application No. PCT/IB2014/061822.

"Energy Harvester For Wireless, Motion and Position-Sensing, Integrating Radiation Sensor for Occupational and Environment Dosimetry", U.S. Appl. No. 14/274,082, filed May 9, 2014.

\* cited by examiner

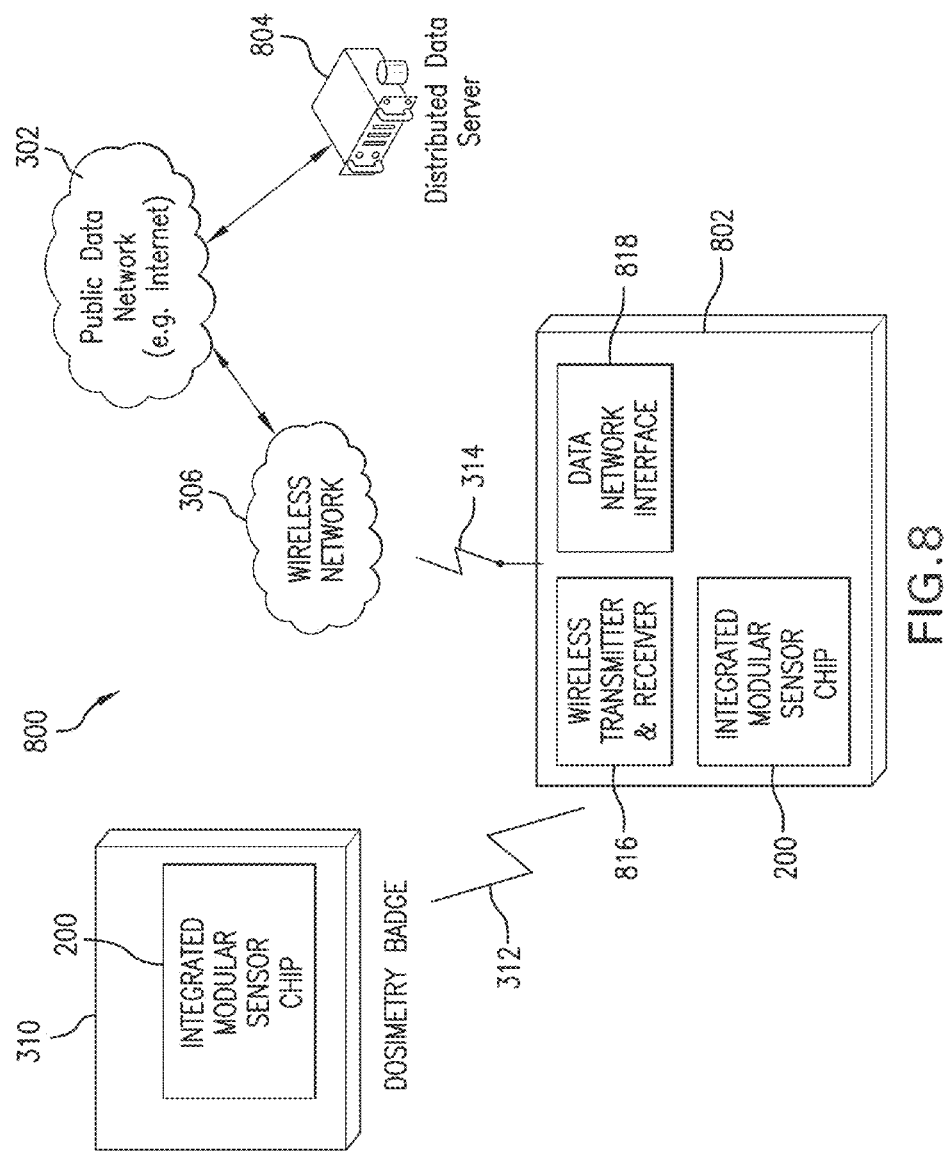

Table 1: MATRIX Computational Procedure.

| STEP | PROCEDURE |
|---|---|
| 1 | INPUT the Dosimeter Element Responses and the Dosimeter Response Matrix for the corresponding Dosimeter Type, and then calculate the Converted Values from disk to memory |
| 2 | Check for Error Conditions |
| 3 | Calculate does values for each source in the Response Matrix |
| 4 | Calculate total reportable doses |
| 5 | Estimate most likely source |
| 6 | Calculate Final (Net) Dose |
| 7 | OUTPUT Net Dose from memory disk |

FIG.9

SYSTEM FOR MOTION AND ACTIVITY CORRELATION WITH DOSE FOR OCCUPATIONAL AND ENVIRONMENTAL DOSIMETRY

CROSS-REFERENCE TO RELATED APPLICATIONS

This application is a divisional application of U.S. patent application Ser. No. 14/289,349 to Valentino et al., entitled "SYSTEM FOR MOTION AND ACTIVITY CORRELATION WITH DOSE FOR OCCUPATIONAL AND ENVIRONMENTAL DOSIMETRY", filed May 28, 2014, which in turn claims benefit of priority to and is a continuation-in-part of U.S. patent application Ser. No. 14/274,082 to Valentino et al., entitled, "ENERGY HARVESTER FOR WIRELESS, MOTION AND POSITION-SENSING, INTEGRATING RADIATION SENSOR FOR OCCUPATIONAL AND ENVIRONMENTAL DOSIMETRY," filed May 9, 2014, now pending, which claims benefit of priority to U.S. Provisional Patent Application No. 61/821,683 filed May 9, 2013 which is incorporated by reference in its entirety. This application claims benefit of priority to and is a continuation-in-part of now U.S. Pat. No. 8,822,924 to Valentino et al., entitled, "WIRELESS, MOTION AND POSITION-SENSING, INTEGRATING RADIATION SENSOR FOR OCCUPATIONAL AND ENVIRONMENTAL DOSIMETRY," filed May 31, 2013, now pending, which claims benefit of priority to U.S. Provisional Patent Application No. 61/654,162 to Valentino et al. entitled, "WIRELESS, MOTION AND POSITION-SENSING, INTEGRATING RADIATION SENSOR FOR OCCUPATIONAL AND ENVIRONMENTAL DOSIMETRY," filed Jun. 1, 2012 which is hereby incorporated by reference in its entirety.

BACKGROUND

1. Field of the Invention

The present invention relates to measuring the motion activity of a person that is being monitored for exposure to a measurable quantity of a potentially hazardous entity or material such as a radiation source, a chemical substance, or a biological agent.

2. Background of the Invention

A problem with respect to radiation sensors that are worn by an individual, such in the form of a personal dosimeter, is that it has been difficult to determine if the individual has been wearing the dosimeter, or how long the individual has been wearing the dosimeter. The correlation of motion activity, time, spatial position, and a measured quantity of hazardous material is critically important in determining if the exposure occurred during the course of normal activity, and if it occurred during working hours at the work location. This information can be used to verify and ensure compliance with occupational monitoring and other regulatory requirements, and to enhance the effectiveness of occupational safety programs.

SUMMARY

According to a first broad aspect, the present invention provides a method comprising the following steps: (a) determining a first period of time that an individual has been active based on motion data for a dosimeter worn by the individual and time data associated with the motion data, and (b) reporting the first period of time the individual has been active via a visual display device and/or via saving the first period of time the individual has been active to a storage medium, wherein the dosimeter comprises one or more motion sensors for generating the motion data.

According to a second broad aspect, the present invention provides a method comprising the following steps: (a) determining whether an individual was wearing a dosimeter during a monitored period based upon motion and time data obtained from the dosimeter, and (b) determining whether an individual was wearing the dosimeter when the dosimeter was exposed to one or more radiation sources based upon measured radiation dosage data for the dosimeter, motion data for the dosimeter, time data associated with the radiation dosage data, and time data associated with the motion data, (c) reporting whether the dosimeter was worn during a monitored period via display on a visual display device and/or via saving whether the individual was wearing a dosimeter when the dosimeter was exposed to one or more radiation sources to a storage medium, wherein the dosimeter comprises one or more motion sensors for generating the motion data, and (d) reporting whether the individual was wearing a dosimeter when the dosimeter was exposed to one or more radiation sources via display on a visual display device and/or via saving whether the individual was wearing a dosimeter when the dosimeter was exposed to one or more radiation doses to a storage medium, wherein the dosimeter comprises one or more motion sensors for generating the motion data.

According to a third broad aspect, the present invention provides a method comprising the following steps: (a) determining a dosimeter was in a location when the dosimeter was exposed to one or more radiation doses based on radiation dosage data for the dosimeter, motion data for the dosimeter, time data associated with the radiation dosage data, time data associated with the motion data, and location data and location data for the dosimeter, and (b) reporting whether the dosimeter was in the location when the dosimeter was exposed to one or more radiation doses via display on a visual display device and/or via saving whether the dosimeter was in the location when the dosimeter was exposed to one or more radiation doses to a storage medium, wherein the dosimeter comprises one or more motion sensors for generating the motion data.

According to a fourth broad aspect, the present invention provides a method comprising the following steps: (a) determining where on a body of an individual that the individual was wearing a dosimeter when the dosimeter was exposed to one or more radiation doses based motion data for the dosimeter and time data associated with the motion data, and (b) reporting where on the body of the individual the individual was wearing a dosimeter when the dosimeter was exposed to one or more radiation doses via display on a visual display device and/or via saving whether the individual was wearing a dosimeter when the dosimeter was exposed to one or more radiation doses to a storage medium, wherein the dosimeter comprises one or more motion sensors for generating the motion data.

According to a fifth broad aspect, the present invention provides a method comprising the following steps: (a) determining a probability that an individual wearing a dosimeter is the individual to whom the dosimeter is assigned based on motion data for the dosimeter, and (b) reporting the probability that the individual wearing the dosimeter is the individual to whom the dosimeter is assigned via display on a visual display device and/or via saving the probability that the individual wearing the dosimeter is the individual to whom the dosimeter is assigned to a storage medium, wherein the dosimeter comprises one or more motion sensors for generating the motion data.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 8 illustrates a wireless sensor base station configuration according to an exemplary embodiment of the present invention;

FIG. 9 illustrates a computational procedure according to an exemplary embodiment of the present invention;

DETAILED DESCRIPTION OF THE PREFERRED EMBODIMENTS

Definitions

Figure 1:
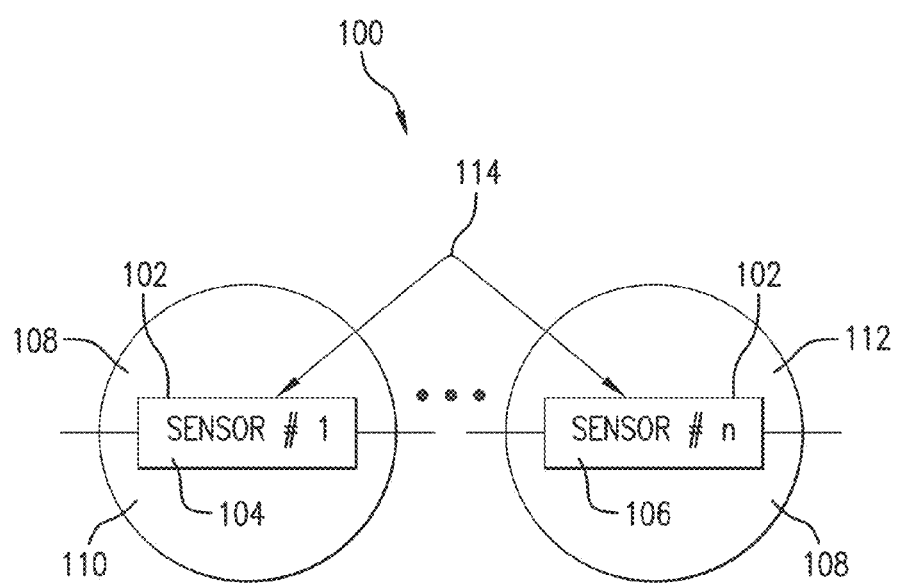
FIG. 1 illustrates a split sphere encapsulating "filtration bubble" for a plurality of ionizing radiation sensors according to an exemplary embodiment of the present invention.

Where the definition of terms departs from the commonly used meaning of the term, applicant intends to utilize the definitions provided below, unless specifically indicated.

For the purposes of the present invention, directional terms such as "top", "bottom", "upper", "lower", "above", "below", "left", "right", "horizontal", "vertical", "upward", "downward", etc., are merely used for convenience in describing the various embodiments of the present invention.

For purposes of the present invention, a value or property is "based" on a particular value, property, the satisfaction of a condition or other factor if that value is derived by performing a mathematical calculation or logical decision using that value, property or other factor.

For the purposes of the present invention, the term "accelerometer" refers to an electromechanical device for measuring acceleration forces including static or dynamic forces. An accelerometer measures proper acceleration, which is the acceleration it experiences relative to free fall and is the acceleration felt by people and objects. Put another way, at any point in space time the equivalence principle guarantees the existence of a local inertial frame, and an accelerometer measures the acceleration relative to that frame. [1] Such accelerations are popularly measured in terms of g-force. Single- and multi-axis models of accelerometer are available to detect magnitude and direction of the proper acceleration (or g-force), as a vector quantity, and can be used to sense orientation (because direction of weight changes), coordinate acceleration (so long as it produces g-force or a change in g-force), vibration, shock, and falling in a resistive medium (a case where the proper acceleration changes, since it starts at zero, then increases). Micro-machined accelerometers are increasingly present in portable electronic devices and video game controllers, to detect the position of the device or provide for game input. Pairs of accelerometers extended over a region of space can be used to detect differences (gradients) in the proper accelerations of frames of references associated with those points. These devices are called gravity gradiometers, as they measure gradients in the gravitational field. Such pairs of accelerometers in theory may also be able to detect gravitational waves.

For purposes of the present invention, the term "active" refers to an individual who is wearing a dosimeter or other type of sensor.

For purposes of the present invention, the term "active time period" refers to the time period that a person is active.

For the purposes of the present invention, the term "angle of incidence" refers to the angle between the direction of the radiation source and a line perpendicular (normal) to the detector surface.

For purposes of the present invention, the term "associated" with respect to data refers to data that are associated or linked to each other. For example, data relating the identity of an individual (identity data) wearing an integrated sensor module may be associated with the motion data for the individual obtained from an accelerometer or, optionally, from a gyroscope or, optionally, from the amplitude of the power signal from an energy harvester.

For the purposes of the present invention, the term "autonomous mobile sensor (AMS) network" refers a network of independently functioning mobile sensors, each capable of moving in response to the intensity of the detected event and their proximity to the other mobile sensors, such that the group of mobile sensors automatically follows the dynamic distribution of the tracked entity as the intensity changes over time or distributes over a geographic region or within a building or structure.

For the purposes of the present invention, the term "ANT" or "ANT+: refers to a proprietary wireless sensor network technology featuring a wireless communications protocol stack that enables semiconductor radios operating in the 2.4 GHz industrial, scientific, and medical allocation of the RF spectrum ("ISM band") to communicate by establishing standard rules for co-existence, data representation, signaling, authentication, and error detection. ANT is characterized by a low computational overhead and low to medium efficiency, resulting in low power consumption by the radios supporting the protocol.

For the purposes of the present invention, the term "Bluetooth®" refers to a wireless technology standard for exchanging data over short distances (using short-wavelength radio transmissions in the ISM band from 2400-2480 MHz) from fixed and mobile devices, creating personal area networks (PANs) with high levels of security. Created by telecom vendor Ericsson in 1994, it was originally conceived as a wireless alternative to RS-232 data cables. It can connect several devices, overcoming problems of synchronization. Bluetooth® is managed by the Bluetooth® Special Interest Group, which has more than 18,000 member companies in the areas of telecommunication, computing, networking, and consumer electronics. Bluetooth® was standardized as IEEE 802.15.1, but the standard is no longer maintained. The SIG oversees the development of the specification, manages the qualification program, and protects the trademarks. To be marketed as a Bluetooth® device, it must be qualified to standards defined by the SIG. A network of patents is required to implement the technology and are licensed only for those qualifying devices.

For the purposes of the present invention, the term a "chemical sensor" refers to a device that measures the presence, concentration or absolute quantity of a given chemical entity, such as an element or molecule, in either a gas, liquid or solid phase.

For the purposes of the present invention, the term "cloud computing" is synonymous with computing performed by computers that are located remotely and accessed via the Internet (the "Cloud"). It is a style of computing where the computing resources are provided "as a service", allowing users to access technology-enabled services "in the cloud" without knowledge of, expertise with, or control over the technology infrastructure that supports them. According to the IEEE Computer Society it "is a paradigm in which information is permanently stored in servers on the Internet and cached temporarily on clients that include desktops, entertainment centers, table computers, notebooks, wall computers, handhelds, etc." Cloud computing is a general concept that incorporates virtualized storage, computing and web services and, often, software as a service (SaaS), where the common theme is reliance on the Internet for satisfying the computing needs of the users. For example, Google Apps provides common business applications online that are accessed from a web browser, while the software and data are stored on the servers. Some successful cloud architectures may have little or no established infrastructure or billing systems whatsoever including Peer-to-peer networks like BitTorrent and Skype and volunteer computing like SETI@home. The majority of cloud computing infrastructure currently consists of reliable services delivered through next-generation data centers that are built on computer and storage virtualization technologies. The services may be accessible anywhere in the world, with the Cloud appearing as a single point of access for all the computing needs of data consumers. Commercial offerings may need to meet the quality of service requirements of customers and may offer service level agreements. Open standards and open source software are also critical to the growth of cloud computing. As customers generally do not own the infrastructure, they are merely accessing or renting, they may forego capital expenditure and consume resources as a service, paying instead for what they use. Many cloud computing offerings have adopted the utility computing model which is analogous to how traditional utilities like electricity are consumed, while others are billed on a subscription basis. By sharing "perishable and intangible" computing power between multiple tenants, utilization rates may be improved (as servers are not left idle) which can reduce costs significantly while increasing the speed of application development. A side effect of this approach is that "computer capacity rises dramatically" as customers may not have to engineer for peak loads. Adoption has been enabled by "increased high-speed bandwidth" which makes it possible to receive the same response times from centralized infrastructure at other sites.

For purposes of the present invention, the term "computer" refers to any type of computer or other device that implements software including an individual computer such as a personal computer, laptop computer, tablet computer, mainframe computer, mini-computer, etc. A computer also refers to electronic devices such as an electronic scientific instrument such as a server, spectrometer, a smartphone, an eBook reader, a cell phone, a television, a handheld electronic game console, a videogame console, a compressed audio or video player such as an MP3 player, a Blu-ray player, a DVD player, etc. In addition, the term "computer" refers to any type of network of computers, such as a network of computers in a business, a computer bank, the Cloud, the Internet, etc. Various processes of the present invention may be carried out using a computer. Various functions of the present invention may be performed by one or more computers.

For the purposes of the present invention, the term "computer hardware" is the digital circuitry and physical devices of a computer system, as opposed to computer software, which is stored on a hardware device such as a hard disk. Most computer hardware is not seen by normal users, because it is embedded within a variety of every day systems, such as in automobiles, microwave ovens, electrocardiograph machines, compact disc players, and video games, among many others. A typical personal computer consists of a case or chassis in a tower shape (desktop) and the following parts: motherboard, CPU, RAM, firmware, internal buses (PIC, PCI-E, USB, HyperTransport, CSI, AGP, VLB), external bus controllers (parallel port, serial port, USB, Firewire, SCSI. PS/2, ISA, EISA, MCA), power supply, case control with cooling fan, storage controllers (CD-ROM, DVD, DVD-ROM, DVD Writer, DVD RAM Drive, Blu-ray, BD-ROM, BD Writer, floppy disk, USB Flash, tape drives, SATA, SAS), video controller, sound card, network controllers (modem, NIC), and peripherals, including mice, keyboards, pointing devices, gaming devices, scanner, webcam, audio devices, printers, monitors, etc.

For the purposes of the present invention, the term "computer network" refers to a group of interconnected computers. Networks may be classified according to a wide variety of characteristics. The most common types of computer networks in order of scale include: Personal Area Network (PAN), Local Area Network (LAN), Campus Area Network (CAN), Metropolitan Area Network (MAN), Wide Area Network (WAN), Global Area Network (GAN), Internetwork (intranet, extranet, Internet), and various types of wireless networks. All networks are made up of basic hardware building blocks to interconnect network nodes, such as Network Interface Cards (NICs), Bridges, Hubs, Switches, and Routers. In addition, some method of connecting these building blocks is required, usually in the form of galvanic cable (most commonly category 5 cable). Less common are microwave links (as in IEEE 802.11) or optical cable ("optical fiber").

For the purposes of the present invention, the term "computer software" refers to a general term used to describe a collection of computer programs, procedures and documentation that perform some tasks on a computer system. The term includes application software such as word processors which perform productive tasks for users, system software such as operating systems, which interface with hardware to provide the necessary services for application software, and middleware which controls and co-ordinates distributed systems. Software may include websites, programs, video games, etc. that are coded by programming languages like C, C++, Java, etc. Computer software is usually regarded as anything but hardware, meaning the "hard" are the parts that are tangible (able to hold) while the "soft" part is the intangible objects inside the computer. Computer software is so called to distinguish it from computer hardware, which encompasses the physical interconnections and devices required to store and execute (or run) the software. At the lowest level, software consists of a machine language specific to an individual processor. A machine language consists of groups of binary values signifying processor instructions which change the state of the computer from its preceding state.

For the purposes of the present invention, the term "computer system" refers to any type of computer system that implements software including an individual computer such as a personal computer, mainframe computer, mini-computer, etc. In addition, computer system refers to any type of network of computers, such as a network of computers in a business, the Internet, personal data assistant (PDA), devices such as a cell phone, a television, a videogame console, a compressed audio or video player such as an MP3 player, a DVD player, a microwave oven, etc. A personal computer is one type of computer system that typically includes the following components: a case or chassis in a tower shape (desktop) and the following parts: motherboard. CPU, RAM, firmware, internal buses (PIC, PCI-E, USB, HyperTransport, CSI, AGP, VLB), external bus controllers (parallel port, serial port, USB. Firewire, SCSI. PS/2, ISA, EISA, MCA), power supply, case control with cooling fan, storage controllers (CD-ROM, DVD, DVD-ROM, DVD Writer, DVD RAM Drive, Blu-ray, BD-ROM, BD Writer, floppy disk, USB Flash, tape drives, SATA, SAS), video controller, sound card, network controllers (modem, NIC), and peripherals, including mice, keyboards, pointing devices, gaming devices, scanner, webcam, audio devices, printers, monitors, etc.

For the purposes of the present invention, the term "data" means the reinterpretable representation of information in a formalized manner suitable for communication, interpretation, or processing. Although one type of common type data is a computer file, data may also be streaming data, a web service, etc. The term "data" is used to refer to one or more pieces of data.

For the purposes of the present invention, the term "database" or "data record" refers to a structured collection of records or data that is stored in a computer system. The structure is achieved by organizing the data according to a database model. The model in most common use today is the relational model. Other models such as the hierarchical model and the network model use a more explicit representation of relationships (see below for explanation of the various database models). A computer database relies upon software to organize the storage of data. This software is known as a database management system (DBMS). Database management systems are categorized according to the database model that they support. The model tends to determine the query languages that are available to access the database. A great deal of the internal engineering of a DBMS, however, is independent of the data model, and is concerned with managing factors such as performance, concurrency, integrity, and recovery from hardware failures. In these areas there are large differences between products.

For the purposes of the present invention, the term "database management system (DBMS)" represents computer software designed for the purpose of managing databases based on a variety of data models. A DBMS is a set of software programs that controls the organization, storage, management, and retrieval of data in a database. DBMS are categorized according to their data structures or types. It is a set of prewritten programs that are used to store, update and retrieve a Database.

For the purposes of the present invention, the term "data storage medium" or "data storage device" refers to any medium or media on which a data may be stored for use by a computer system. Examples of data storage media include floppy disks, Zip™ disks, CD-ROM, CD-R, CD-RW, DVD, DVD-R, memory sticks, flash memory, hard disks, solid state disks, optical disks, etc. Two or more data storage media acting similarly to a single data storage medium may be referred to as a "data storage medium" for the purposes of the present invention. A data storage medium may be part of a computer.

For the purposes of the present invention, the term "dosimeter" refers to a device for measuring an individual's or an object's exposure to something in the environment—particularly to a hazard inflicting cumulative impact over long periods of time, or over a lifetime. A radiation dosimeter measures exposure to ionizing radiation. The radiation dosimeter is of fundamental importance in the disciplines of radiation dosimetry and health physics. Other types of dosimeters are sound dosimeters, ultraviolet dosimeters and electromagnetic field dosimeters. Ionizing radiation, such as X-rays, alpha rays, beta rays, and gamma rays, are undetectable by the human senses, therefore a measuring device, such as a dosimeter, is used to detect, measure and record this, and in some cases give an alarm when a preset level is exceeded. Ionizing radiation damage to the body is cumulative, and is related to the total dose received, for which the SI unit is the sievert. Therefore, workers exposed to radiation, such as radiographers, nuclear power plant workers, doctors, physicists and radiation therapists employing radiotherapy machines, those in laboratories using radionuclides, and some HAZMAT teams are required to wear dosimeters so their employers can keep a record of their exposure to verify that it is below legally prescribed limits. Such devices may be recognized as "legal dosimeters," meaning that they have been approved for use in recording personnel dose for regulatory purposes.

For the purposes of the present invention, the term "energy compensating material" refers to a material that when placed between an OSLM and a source of gamma radiation or x-ray radiation alters the response over a range of gamma energies or x-ray energies compared to the OSLM exposed with no compensating or filtering material. Examples of energy compensating materials are copper and aluminum.

For the purposes of the present invention, the term "flocking-algorithm" refers to an computational procedure that allows a network of mobile sensors to move as a function of each sensor's proximity to other mobile sensors as well as the intensity or amplitude of a measured event, such that the network of mobile sensors moves autonomously in a concerted, self-organized fashion that tracks the dynamic motion and distribution of the measured event.

For purposes of the present invention, the term "hardware and/or software" refers to functions that may be performed by computer software, computer hardware, or a combination of both computer hardware and computer software. Various features of the present invention may be performed by hardware and/or software.

For purposes of the present invention, the term "individual" refers to an individual mammal, such as a human being.

For the purposes of the present invention, the term "Internet" is a global system of interconnected computer networks that interchange data by packet switching using the standardized Internet Protocol Suite (TCP/IP). It is a "network of networks" that consists of millions of private and public, academic, business, and government networks of local to global scope that are linked by copper wires, fiber-optic cables, wireless connections, and other technologies. The Internet carries various information resources and services, such as electronic mail, online chat, file transfer and file sharing, online gaming, and the inter-linked hypertext documents and other resources of the World Wide Web (WWW).

For the purposes of the present invention, the term "Internet protocol (IP)" refers to a protocol used for communicating data across a packet-switched internetwork using the Internet Protocol Suite (TCP/IP). IP is the primary protocol in the Internet Layer of the Internet Protocol Suite and has the task of delivering datagrams (packets) from the source host to the destination host solely based on its address. For this purpose the Internet Protocol defines addressing methods and structures for datagram encapsulation. The first major version of addressing structure, now referred to as Internet Protocol Version 4 (Ipv4) is still the dominant protocol of the Internet, although the successor, Internet Protocol Version 6 (Ipv6) is actively deployed world-wide. In one embodiment, an EGI-SOA of the present invention may be specifically designed to seamlessly implement both of these protocols.

For the purposes of the present invention, the term "intranet" refers to a set of networks, using the Internet Protocol and IP-based tools such as web browsers and file transfer applications that are under the control of a single administrative entity. That administrative entity closes the intranet to all but specific, authorized users. Most commonly, an intranet is the internal network of an organization. A large intranet will typically have at least one web server to provide users with organizational information. Intranets may or may not have connections to the Internet. If connected to the Internet, the intranet is normally protected from being accessed from the Internet without proper authorization. The Internet is not considered to be a part of the intranet.

For the purposes of the present invention, the term "ionizing radiation" refers to any particulate or electromagnetic radiation that is capable of dissociating atoms into a positively and negatively charged ion pair. The present invention may be used to determine doses of both directly ionizing radiation and indirectly ionizing radiation. Ionizing (or ionising) radiation is radiation composed of particles that individually carry enough kinetic energy to liberate an electron from an atom or molecule, ionizing it. Ionizing radiation is generated through nuclear reactions, either artificial or natural, by very high temperature (e.g., plasma discharge or the corona of the Sun), via production of high energy particles in particle accelerators, or due to acceleration of charged particles by the electromagnetic fields produced by natural processes, from lightning to supernova explosions. When ionizing radiation is emitted by or absorbed by an atom, it can liberate an atomic particle (typically an electron, proton, or neutron, but sometimes an entire nucleus) from the atom. Such an event can alter chemical bonds and produce ions, usually in ion-pairs, that are especially chemically reactive. This greatly magnifies the chemical and biological damage per unit energy of radiation because chemical bonds will be broken in this process. If the atom was inside a crystal lattice in a solid phase, then a "hole" will exist where the original atom was. Ionizing radiation includes cosmic rays, Alpha particles, Beta particles, Gamma rays, X-rays, and in general any charged particle moving at relativistic speeds. Neutrons are considered ionizing radiation at any speed. Ionizing radiation includes some portion of the ultraviolet spectrum, depending on context. Radio waves, microwaves, infrared light, and visible light are normally considered non-ionizing radiation, although very high intensity beams of these radiations can produce sufficient heat to exhibit some similar properties to ionizing radiation, by altering chemical bonds and removing electrons from atoms. Ionizing radiation is ubiquitous in the environment, and comes from naturally occurring radioactive materials and cosmic rays. Common artificial sources are artificially produced radioisotopes, X-ray tubes and particle accelerators. Ionizing radiation is invisible and not directly detectable by human senses, so instruments such as Geiger counters are usually required to detect its presence. In some cases it may lead to secondary emission of visible light upon interaction with matter, such as in Cherenkov radiation and radioluminescence. It has many practical uses in medicine, research, construction, and other areas, but presents a health hazard if used improperly. Exposure to ionizing radiation causes damage to living tissue, and can result in mutation, radiation sickness, cancer, and death.

For the purposes of the present invention, the term "ionizing radiation sensor" refers to a device that measures the presence or activity of a material or substance that emits or generates ionizing radiation.

For the purposes of the present invention, the term "irradiation" refers to the conventional meaning of the term "irradiation", i.e., exposure to high energy charge particles, e.g., electrons, protons, alpha particles, etc., or electromagnetic radiation of wave-lengths shorter than those of visible light, e.g., gamma rays, x-rays, ultraviolet, etc.

For purposes of the present invention, the term "linked type of motion" refers to one type of motion causing a second type of motion. For example, a walking motion by an individual is one type of motion and may cause a linked second type of motion, i.e., a pendulum motion of any individual's wrist. A running motion by an individual is also one type of motion and may cause a second linked type of motion, i.e., a cyclic motion at the individual's wrist later to a direction detected by a motion sensor.

For the purposes of the present invention, the term "local area network (LAN)" refers to a network covering a small geographic area, like a home, office, or building. Current LANs are most likely to be based on Ethernet technology. The cables to the servers are typically on Cat 5e enhanced cable, which will support IEEE 802.3 at 1 Gbit/s. A wireless LAN may exist using a different IEEE protocol, 802.11b, 802.11g or possibly 802.11n. The defining characteristics of LANs, in contrast to WANs (wide area networks), include their higher data transfer rates, smaller geographic range, and lack of a need for leased telecommunication lines. Current Ethernet or other IEEE 802.3 LAN technologies operate at speeds up to 10 Gbit/s.

For purposes of the present invention, the term "location data" and the term "position data" refer to data about the location of an individual or an object, such as a dosimeter. Location data may be generated using a position beacon, a GPS device, etc.

For the purposes of the current invention, the term "low powered wireless network" refers to an ultra-low powered wireless network between sensor nodes and a centralized device. The ultra-low power is needed by devices that need to operate for extended periods of time from small batteries energy scavenging technology. Examples of low powered wireless networks are ANT, ANT+, Bluetooth Low Energy (BLE), ZigBee and WiFi.

For purposes of the present invention, the term "machine-readable medium" refers to any tangible or non-transitory medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" includes, but is limited to, solid-state memories, and optical and magnetic media. Specific examples of machine-readable media include non-volatile memory, including by way of example, semiconductor memory devices, e.g., EPROM, EEPROM, and flash memory devices; magnetic disks such as internal hard disks and removable disks; magneto-optical disks; and CD-ROM and DVD-ROM disks. The term "machine-readable medium" may include a single medium or multiple media (e.g., a centralized or distributed database, and/or associated caches and servers) that store the one or more instructions or data structures. A machine-readable medium may be part of a computer.

For the purposes of the present invention, the term "MEMS" refers to Micro-Electro-Mechanical Systems. MEMS, is a technology that in its most general form may be defined as miniaturized mechanical and electro-mechanical elements (i.e., devices and structures) that are made using the techniques of microfabrication. The critical physical dimensions of MEMS devices can vary from well below one micron on the lower end of the dimensional spectrum, all the way to several millimeters. Likewise, the types of MEMS devices can vary from relatively simple structures having no moving elements, to extremely complex electromechanical systems with multiple moving elements under the control of integrated microelectronics. A main criterion of MEMS may include that there are at least some elements having some sort of mechanical functionality whether or not these elements can move. The term used to define MEMS varies in different parts of the world. In the United States they are predominantly called MEMS, while in some other parts of the world they are called "Microsystems Technology" or "micromachined devices." While the functional elements of MEMS are miniaturized structures, sensors, actuators, and microelectronics, most notable elements may include microsensors and microactuators. Microsensors and microactuators may be appropriately categorized as "transducers," which are defined as devices that convert energy from one form to another. In the case of microsensors, the device typically converts a measured mechanical signal into an electrical signal.

For the purposes of the present invention the term "mesh networking" refers to a type of networking where each node must not only capture and disseminate its own data, but also serve as a relay for other nodes, that is, it must collaborate to propagate the data in the network. A mesh network can be designed using a flooding technique or a routing technique. When using a routing technique, the message is propagated along a path, by hopping from node to node until the destination is reached. To ensure all its paths' availability, a routing network must allow for continuous connections and reconfiguration around broken or blocked paths, using self-healing algorithms. A mesh network whose nodes are all connected to each other is a fully connected network. Mesh networks can be seen as one type of ad hoc network. Mobile ad hoc networks and mesh networks are therefore closely related, but mobile ad hoc networks also have to deal with the problems introduced by the mobility of the nodes. The self-healing capability enables a routing based network to operate when one node breaks down or a connection goes bad. As a result, the network is typically quite reliable, as there is often more than one path between a source and a destination in the network. Although mostly used in wireless situations, this concept is also applicable to wired networks and software interaction.

For the purposes of the present invention the term "microfluidics" refers to a branch micro-fabrication which is concerned with developing means of handling small volumes of liquids. An aspect of the present invention is to utilize fluidic structures consisting of a large number of microscopic volumes of liquids (e.g., volumes from picoliters to microliters) as a working element in a mechanical-to electrical energy conversion system. The large number of these microscopic elements (on the order of hundreds or even thousands) yields a realistic amount of electrical energy that can be generated from a relatively small volume of mechanical motion.

For the purposes of the present invention the term "mobile ad hoc network" is a self-configuring infrastructureless network of mobile devices connected by wireless. Ad hoc is Latin and means "for this purpose". Each device in a mobile ad hoc network is free to move independently in any direction, and will therefore change its links to other devices frequently. Each must forward traffic unrelated to its own use, and therefore be a router. The primary challenge in building a mobile ad hoc network is equipping each device to continuously maintain the information required to properly route traffic. Such networks may operate by themselves or may be connected to the larger Internet. Mobile ad hoc networks are a kind of wireless ad hoc networks that usually has a routable networking environment on top of a Link Layer ad hoc network. The growths of laptops and wireless networks have made mobile ad hoc networks a popular research topic since the mid-1990s. Many academic papers evaluate protocols and their abilities, assuming varying degrees of mobility within a bounded space, usually with all nodes within a few hops of each other. Different protocols are then evaluated based on measure such as the packet drop rate, the overhead introduced by the routing protocol, end-to-end packet delays, network throughput etc.

For purposes of the present invention, the term "motion data" and the term "motion activity data" refer to data relating to the motion of an individual, an object or a device and to the motion of any part of an individual, an object or a device. Motion data may have associated time data relating to when motion started, when motion stopped, the duration of motion, etc.

For the purposes of the present invention, the term "network hub" refers to an electronic device that contains multiple ports. When a packet arrives at one port, it is copied to all the ports of the hub for transmission. When the packets are copied, the destination address in the frame does not change to a broadcast address. It does this in a rudimentary way, it simply copies the data to all of the Nodes connected to the hub. This term is also known as hub. The term "Ethernet hub," "active hub." "network hub," "repeater hub." "multiport repeater" or "hub" may also refer to a device for connecting multiple Ethernet devices together and making them act as a single network segment. It has multiple input/output (I/O) ports, in which a signal introduced at the input of any port appears at the output of every port except the original incoming. A hub works at the physical layer (layer 1) of the OSI model. The device is a form of multiport repeater. Repeater hubs also participate in collision detection, forwarding a jam signal to all ports if it detects a collision.

For purposes of the present invention, the term "on-board" refers to a component, such as a motion sensor, GPS device, etc. that is on the same printed circuit board as one or more radiation sensors of an integrated sensor module of the present invention.

For purposes of the present invention, the term "processor" refers to a device that performs the basic operations in a computer. A microprocessor is one example of a processor.

For the purposes of the present invention, the term "radiation attenuating material" refers to a material that reduces the intensity of incident radiation by absorbing some or all of the energy of the radiation within the material.

For purposes of the present invention, the term "radiation dosage data" refers to data based on the exposure of a radiation dosimeter to one or doses of radiation. Time data may be associated with radiation dosage data. For example, a time period when the radiation dosimeter is exposed to one or more doses of radiation.

For the purposes of the present invention, the term "radiation dosimetry" refers to the conventional meaning of the term "radiation dosimetry", i.e., the measurement of the amount of radiation dose absorbed in a material, an object or the body of an individual.

For the purposes of the present invention, the term "radiation sensing material" refers to a material used to sense radiation in a radiation sensor. Examples of radiation sensitive materials including optically stimulated luminescent materials for OSL sensors, thermoluminescent materials for thermoluminescent dosimetry (TLD) sensors, etc.

For the purposes of the present invention, the term "random-access memory (RAM)" refers to a type of computer data storage. Today it takes the form of integrated circuits that allow the stored data to be accessed in any order, i.e. at random. The word random thus refers to the fact that any piece of data can be returned in a constant time, regardless of its physical location and whether or not it is related to the previous piece of data. This contrasts with storage mechanisms such as tapes, magnetic discs and optical discs, which rely on the physical movement of the recording medium or a reading head. In these devices, the movement takes longer than the data transfer, and the retrieval time varies depending on the physical location of the next item. The word RAM is mostly associated with volatile types of memory (such as DRAM memory modules), where the information is lost after the power is switched off. However, many other types of memory are RAM as well, including most types of ROM and a kind of flash memory called NOR-Flash.

For the purposes of the present invention, the term "read-only memory (ROM)" refers to a class of storage media used in computers and other electronic devices. Because data stored in ROM cannot be modified (at least not very quickly or easily), it is mainly used to distribute firmware (software that is very closely tied to specific hardware, and unlikely to require frequent updates). In its strictest sense, ROM refers only to mask ROM (the oldest type of solid state ROM), which is fabricated with the desired data permanently stored in it, and thus can never be modified. However, more modern types such as EPROM and flash EEPROM can be erased and re-programmed multiple times; they are still described as "read-only memory" because the reprogramming process is generally infrequent, comparatively slow, and often does not permit random access writes to individual memory locations.

For the purposes of the present invention, the term "real-time processing" refers to a processing system designed to handle workloads whose state is constantly changing. Real-time processing means that a transaction is processed fast enough for the result to come back and be acted on as transaction events are generated. In the context of a database, real-time databases are databases that are capable of yielding reliable responses in real-time.

For the purposes of the present invention, the term "router" refers to a networking device that forwards data packets between networks using headers and forwarding tables to determine the best path to forward the packets. Routers work at the network layer of the TCP/IP model or layer 3 of the OSI model. Routers also provide interconnectivity between like and unlike media devices. A router is connected to at least two networks, commonly two LANs or WANs or a LAN and its ISP's network.

For the purposes of the present invention, the term "sensor" refers to a collector and/or producer of information and/or data. A sensor can be an instrument or a living organism (e.g. a person). For example, a sensor may be a position locating sensor such as a GPS device, a thermometer, a mobile phone, an individual writing a report, etc. A sensor is an entity capable of observing a phenomenon and returning an observed value. For example, a mercury thermometer converts the measured temperature into expansion and contraction of a liquid which can be read on a calibrated glass tube. A thermocouple converts temperature to an output voltage which can be read by a voltmeter. For accuracy, all sensors are often be calibrated against known standards. A sensor may include a device which detects or measures a physical property and records, indicates, or responds to that physical property.

For the purposes of the present invention, the term "server" refers to a system (software and suitable computer hardware) that responds to requests across a computer network to provide, or help to provide, a network service. Servers can be run on a dedicated computer, which is also often referred to as "the server," but many networked computers are capable of hosting servers. In many cases, a computer can provide several services and have several servers running. Servers may operate within a client-server architecture and may comprise computer programs running to serve the requests of other programs—the clients. Thus, the server may perform some task on behalf of clients. The clients typically connect to the server through the network but may run on the same computer. In the context of Internet Protocol (IP) networking, a server is a program that operates as a socket listener. Servers often provide essential services across a network, either to private users inside a large organization or to public users via the Internet. Typical computing servers are database server, file server, mail server, print server, web server, gaming server, application server, or some other kind of server. Numerous systems use this client/server networking model including Web sites and email services. An alternative model, peer-to-peer networking may enable all computers to act as either a server or client as needed.

For the purposes of the present invention, the term "solid-state electronics" refers to those circuits or devices built entirely from solid materials and in which the electrons, or other charge carriers, are confined entirely within the solid material. The term is often used to contrast with the earlier technologies of vacuum and gas-discharge tube devices and it is also conventional to exclude electro-mechanical devices (relays, switches, hard drives and other devices with moving parts) from the term solid state. While solid-state can include crystalline, polycrystalline and amorphous solids and refer to electrical conductors, insulators and semiconductors, the building material is most often a crystalline semiconductor. Common solid-state devices include transistors, microprocessor chips, and RAM. A specialized type of RAM called flash RAM is used in flash drives and more recently, solid state drives to replace mechanically rotating magnetic disc hard drives. More recently, the integrated circuit (IC), the light-emitting diode (LED), and the liquid-crystal display (LCD) have evolved as further examples of solid-state devices. In a solid-state component, the current is confined to solid elements and compounds engineered specifically to switch and amplify it.

For the purposes of the present invention, the term "solid state sensor" refers to sensor built entirely from a solid-phase material such that the electrons or other charge carriers produced in response to the measured quantity stay entirely with the solid volume of the detector, as opposed to gas-discharge or electro-mechanical sensors. Pure solid-state sensors have no mobile parts and are distinct from electro-mechanical transducers or actuators in which mechanical motion is created proportional to the measured quantity.

For purposes of the present invention, the term the term "storage medium" refers to any form of storage that may be used to store bits of information. Examples of storage include both volatile and non-volatile memories such as MRRAM, MRRAM, ERAM, flash memory, RFID tags, floppy disks, Zip™ disks, CD-ROM, CD-R, CD-RW, DVD, DVD-R, flash memory, hard disks, optical disks, etc. Two or more storage media acting similarly to a single data storage medium may be referred to as a "storage medium" for the purposes of the present invention. A storage medium may be part of a computer.

For the purposes of the present invention, the term "transmission control protocol (TCP)" refers to one of the core protocols of the Internet Protocol Suite. TCP is so central that the entire suite is often referred to as "TCP/IP." Whereas IP handles lower-level transmissions from computer to computer as a message makes its way across the Internet, TCP operates at a higher level, concerned only with the two end systems, for example a Web browser and a Web server. In particular, TCP provides reliable, ordered delivery of a stream of bytes from one program on one computer to another program on another computer. Besides the Web, other common applications of TCP include e-mail and file transfer. Among its management tasks, TCP controls message size, the rate at which messages are exchanged, and network traffic congestion.

For the purposes of the present invention, the term "time" refers to a component of a measuring system used to sequence events, to compare the durations of events and the intervals between them, and to quantify the motions of objects. Time is considered one of the few fundamental quantities and is used to define quantities such as velocity. An operational definition of time, wherein one says that observing a certain number of repetitions of one or another standard cyclical event (such as the passage of a free-swinging pendulum) constitutes one standard unit such as the second, has a high utility value in the conduct of both advanced experiments and everyday affairs of life. Temporal measurement has occupied scientists and technologists, and was a prime motivation in navigation and astronomy. Periodic events and periodic motion have long served as standards for units of time. Examples include the apparent motion of the sun across the sky, the phases of the moon, the swing of a pendulum, and the beat of a heart. Currently, the international unit of time, the second, is defined in terms of radiation emitted by cesium atoms.

For purposes of the present invention, the term "time data" refers to data relating to time. Time data may be associated with other types of data, such as motion data. For example, motion data may have associated time data relating to when motion started, when motion stopped, the duration of motion, etc. Time data may be generated in a number of ways in the present invention. For example, time data may be generated by: a clock that is part of a radiation sensor device, a hardware or software clock that is part of a processor that is part of the radiation sensor device, a hardware or software clock that is part of a computer that processes data from the radiation sensor, etc.

For the purposes of the present invention, the term "timestamp" refers to a sequence of characters, denoting the date and/or time at which a certain event occurred. This data is usually presented in a consistent format, allowing for easy comparison of two different records and tracking progress over time; the practice of recording timestamps in a consistent manner along with the actual data is called timestamping. Timestamps are typically used for logging events, in which case each event in a log is marked with a timestamp. In file systems, timestamp may mean the stored date/time of creation or modification of a file. The International Organization for Standardization (ISO) has defined ISO 8601 which standardizes timestamps.

For purposes of the present invention, the term "type of motion" refers to a type of motion by all or part of the body of an individual. For example, a walking motion by an individual is one type of motion and may cause a second type of motion, i.e., a pendulum motion of any individual's wrist. A running motion by an individual is also one type of motion and may cause a second type of motion, i.e., a cyclic motion at the individual's wrist later to a direction detected by one or more motion sensors. The motion of a motorized vehicle is another type of motion and may cause secondary and tertiary types of motion, i.e., the forward motion of the vehicle, the vibratory oscillation of the vehicle and the individual in the vehicle, and the periodic motion of the individual's body during the normal course of operating the vehicle. A lack of motion is also considered as one type of motion and may be due, for example, to removing the dosimeter from the individual participant and placing it in a desk, on a table top, or on a fixed structure designed to act as a holder for the dosimeter.

For the purposes of the present invention, the term "visual display device" or "visual display apparatus" includes any type of visual display device or apparatus such as a CRT monitor, LCD screen, LEDs, a projected display, a printer for printing out an image such as a picture and/or text, etc. A visual display device may be a part of another device such as a computer monitor, television, projector, telephone, cell phone, smartphone, laptop computer, tablet computer, handheld music and/or video player, personal data assistant (PDA), handheld game player, head mounted display, a heads-up display (HUD), a global positioning system (GPS) receiver, automotive navigation system, dashboard, watch, microwave oven, electronic organ, automatic teller machine (ATM) etc.

For the purposes of the present invention, the term "web service" refers to the term defined by the W3C as "a software system designed to support interoperable machine-to-machine interaction over a network". Web services are frequently just web APIs that can be accessed over a network, such as the Internet, and executed on a remote system hosting the requested services. The W3C Web service definition encompasses many different systems, but in common usage the term refers to clients and servers that communicate using XML messages that follow the SOAP standard. In such systems, there is often machine-readable description of the operations offered by the service written in the Web Services Description Language (WSDL). The latter is not a requirement of a SOAP endpoint, but it is a prerequisite for automated client-side code generation in many Java and .NET SOAP frameworks. Some industry organizations, such as the WS-I, mandate both SOAP and WSDL in their definition of a Web service. More recently, RESTful Web services have been used to better integrate with HTTP compared to SOAP-based services. They do not require XML messages or WSDL service-API definitions.

For the purposes of the present invention, the term "wide area network (WAN)" refers to a data communications network that covers a relatively broad geographic area (i.e. one city to another and one country to another country) and that often uses transmission facilities provided by common carriers, such as telephone companies. WAN technologies generally function at the lower three layers of the OSI reference model: the physical layer, the data link layer, and the network layer.

For purposes of the present invention, the term "designated work period" refers to a period of time that a person is scheduled to be at work.

For the purposes of the present invention, the term "World Wide Web Consortium (W3C)" refers to the main international standards organization for the World Wide Web (abbreviated WWW or W3). It is arranged as a consortium where member organizations maintain full-time staff for the purpose of working together in the development of standards for the World Wide Web. W3C also engages in education and outreach, develops software and serves as an open forum for discussion about the Web. W3C standards include: CSS, CGI, DOM, GRDDL, HTML, OWL, RDF, SVG, SISR, SOAP, SMIL, SRGS, SSML, VoiceXML, XHTML+Voice, WSDL, XACML. XHTML, XML, XML Events, Xforms, XML Information, Set, XML Schema, Xpath, Xquery and XSLT.

For the purposes of the present invention, the term "Zig-Bee" refers a specification for a suite of high level communication protocols used to create personal area networks built from small, low-power digital radios. ZigBee is based on an IEEE 802 standard. Though low-powered, ZigBee devices often transmit data over longer distances by passing data through intermediate devices to reach more distant ones, creating a mesh network; i.e., a network with no centralized control or high-power transmitter/receiver able to reach all of the networked devices. The decentralized nature of such wireless ad-hoc networks make them suitable for applications where a central node can't be relied upon. ZigBee may be used in applications that require a low data rate, long battery life, and secure networking. ZigBee has a defined rate of 250 kbit/s, best suited for periodic or intermittent data or a single signal transmission from a sensor or input device. Applications include wireless light switches, electrical meters with in-home-displays, traffic management systems, and other consumer and industrial equipment that requires short-range wireless transfer of data at relatively low rates. The technology defined by the ZigBee specification is intended to be simpler and less expensive than other WPANs, such as Bluetooth® or Wi-Fi. Zigbee networks are secured by 128 bit encryption keys.

DESCRIPTION

In existing passive, integrating radiation monitoring devices, such as film, TLD or OSL sensors, incident radiation is accumulated and stored within the molecular structure of the sensor without any need of electrical power. This characteristic makes passive sensors ideal for situations where the risk of a power interruption is unacceptable. Multiple radiation sensors are generally mounted in a holder containing one or more filters that alter the amounts, energies and types of radiation able to reach the sensors. These filters typically sandwich the sensors to achieve correct assessments when the radiation enters the dosimeter from various angles of incidence. To analyze the sensors, they must be removed from between the filters and the holder and physically presented to the processing system required to elicit the quantitative attribute exhibited by the sensor following exposure to radiation.

Radiation dosimeters based on optically stimulated luminescence (OSL) utilize an optical path whereby a stimulating beam of light can illuminate the OSL sensor(s) and the resultant radiation induced luminescence can be routed back through the same or alternate optical path to a light detector such as a photomultiplier tube that quantifies the amount of luminescent light. For more information on OSL materials and systems, see, U.S. Pat. No. 5,731,590 issued to Miller; U.S. Pat. No. 6,846,434 issued to Akselrod; U.S. Pat. No. 6,198,108 issued to Schweitzer et al.; U.S. Pat. No. 6,127,685 issued to Yoder et al.; U.S. patent application Ser. No. 10/768, 094 filed by Akselrod et al.; all of which are incorporated herein by reference in their entireties. See also Optically Stimulated Luminescence Dosimetry. Lars Botter-Jensen et al. Elesevier, 2003; Klemic, G., Bailey, P., Miller. K., Monetti, M. External radiation dosimetry in the aftermath of radiological terrorist event, Rad. Prot. Dosim., in press; Akselrod, M. S., Kortov, V. S., and Gorelova, E. A., Preparation and properties of Al2O3:C, Radiat. Prot. Dosim. 47, 159-164 (1993); and Akselrod, M. S., Lucas, A. C., Polf, J. C., McKeever, S. W. S. Optically stimulated luminescence of Al2O3:C. Radiation Measurements, 29, (3-4), 391-399 (1998), all of which are incorporated herein by reference in their entireties.

Personnel dosimeters are expected to move relative to an exposure source during working hours (the monitoring period) as the individual wearing the dosimeter (the participant) moves during the normal course of performing the monitored activities. Dosimeters that remain stationary or static for extended periods of time cannot be in use and, if the dosimeter should have been in use during a monitored period, then the participant is out of compliance.

Furthermore, if a dosimeter is exposed in the static state, then that would be an abnormal occupational exposure that might occur, for example, if the participant was not. However, if a dosimeter is exposed during normal motion, then that would provide evidence of a routine, as opposed to abnormal, occupational exposure.

In one embodiment, the present invention apparatus and system consisting of multiple sensor devices (including one or more passive, integrating electronic radiation sensors, a MEMS accelerometer, a wireless transmitter and, optionally, a GPS or other positional or locational device, a thermistor, or other chemical, biological or EMF sensors) and computer algorithms and programs for calculating the dose from the event (e.g., the personal dose equivalent), and for the simultaneous detection and wireless transmission of ionizing radiation, motion and global position for use in occupational and environmental dosimetry. The present invention is a new embodiment of existing sensors in a unique new product using new processes and algorithms to create a self-contained, passive, integrating dosimeter that constructs a unique record of event intensity, location, time of the event, temperature and other specialized sensor data such as biological or chemical measurements.

Accordingly, aspects of the disclosed invention provide the use of MEMS and nanotechnology manufacturing techniques to encapsulate individual ionizing radiation sensor elements within a radiation attenuating material that provides a "filtration bubble" around the sensor element, the use of multiple attenuating materials (filters) around multiple sensor elements, and the use of a software algorithm to discriminate between different types of ionizing radiation and different radiation energy.

In one embodiment, the present invention employs the concept of an "exposure event" or a "dose event" as the correlation in time and in spatial location with the measurement of a source of hazardous material, such as a radiation source, a hazardous chemical substance, or a biological agent. In one embodiment, the present invention provides a method and apparatus for determining motion activity events by analysis of motion, time and dose information collected during the exposure event.

In one embodiment of the present invention, motion activity (motion data) is obtained by analysis of the displacement output from an accelerometer or, optionally, the rotational displacement output from a gyroscope or, optionally, the power signature from an energy harvester or, optionally, other sensors that produce an output signal whose amplitude varies as a function of motion.

In one embodiment of the present invention, position information (location data) is obtained from wireless communication systems such as wireless base stations or hubs or, optionally, from other wireless devices that communicate spatial positioning information such as Bluetooth location beacons or, optionally, from a global positioning system (GPS).

In one embodiment of the present invention, exposure information is obtained from one or more sensors, which may include non-ionizing radiation such as UV or infrared light, ionizing radiation such as beta radiation, x-rays or gamma-rays, chemical substances such as hazardous liquids or gasses, or biological agents such as infectious bacteria, viruses, mold or other types of fungus or microbes.

In one embodiment of the present invention, time information is obtained from an on-board clock.

In one embodiment of the present invention, additional information that is useful in characterizing exposure events may be obtained from other on-board sensors such as temperature, pressure or humidity sensors.

As shown in FIG. 1, an exemplary sensor array 100 comprising MEMS and nanotechnology manufacturing techniques are employed to create a configuration of encapsulating radiation attenuating material around respective nanoscale radiation sensors. As illustrated, a plurality of ionizing radiation sensors 102 are provided and configurable, for example, to be integrated on electronic chip circuitry, as discussed below. Ionizing radiation sensors 102 may include solid state sensor technology including a detecting surface 114 of the sensor.

Ionizing radiation sensors 102 may be arranged into modular sensor arrays 204 (FIG. 2) comprising one or more radiation sensors 102 and mounted on a printed circuit board (PCB), for example, as described below.

FIG. 1 illustrates a first sensor 104 encapsulated, for example, in a filter material such as a specific radiation attenuating material 108 or a "filtration bubble" 110 having, for example, a prescribed thickness. Up to "n" sensors 106 may be manufactured and encapsulated in up to "n" different respective filtration bubbles 112, where each filtration bubble can consist of a similar or different materials or similar or different material thicknesses. In this example, filtration bubble 108 corresponds to sensor 106 such that sensor 106 is surrounded or encapsulated by filtration bubble 108. In some preferred embodiments, the filtration bubble may comprise a spherical geometry, or a rectilinear or other geometry to cover the sensor to provide an optimal angular response wherein the response of the sensor is independent of the angle of incidence of the radiation or other measured quantity, such that the output of sensor 106 is the same at any angle (i.e., the filter is designed to produce a "flat" response at any angle). Materials of the filtration bubble may include thin metallic layers including, for example, copper, tin, aluminum, tungsten, etc. The filtration bubble will characteristically be comprised of radiation attenuating material(s) capable of filtering out, for example, alpha particles and beta radiation. Filter material such as specific radiation attenuating material 108 or a "filtration bubble" provides an optimal angular response wherein the response of the sensor is independent of the angle of incidence of the radiation (or other measured quantity), i.e., the output of sensor 106 is the same (or "flat") at all angles.

Additional aspects of the disclosed invention provide the use of MEMS and nanotechnology sensors to simultaneously detect motion, global position, radiation exposure, and a process, such as the use of a software algorithm, to correlate radiation exposure levels over time with motion of the detector and with the global position of the detector. Accordingly, features of disclosed embodiments enable, at least, the following advantages: (1) providing the correlation of radiation exposure levels with time, motion and global position of the detector to provide unique and valuable information on how the exposure occurred; (2) allowing the global position to detect either via an on-board position locating sensor, such as a GPS sensor, or by a connected external electrical device, such as a mobile smart device (e.g., smartphone), with a built-in GPS sensor or by estimation from a mesh of networked devices; (3) providing enablement such that the time, motion and global position can be optionally recorded when the detected exposure exceeds a threshold level.

Figure 2:
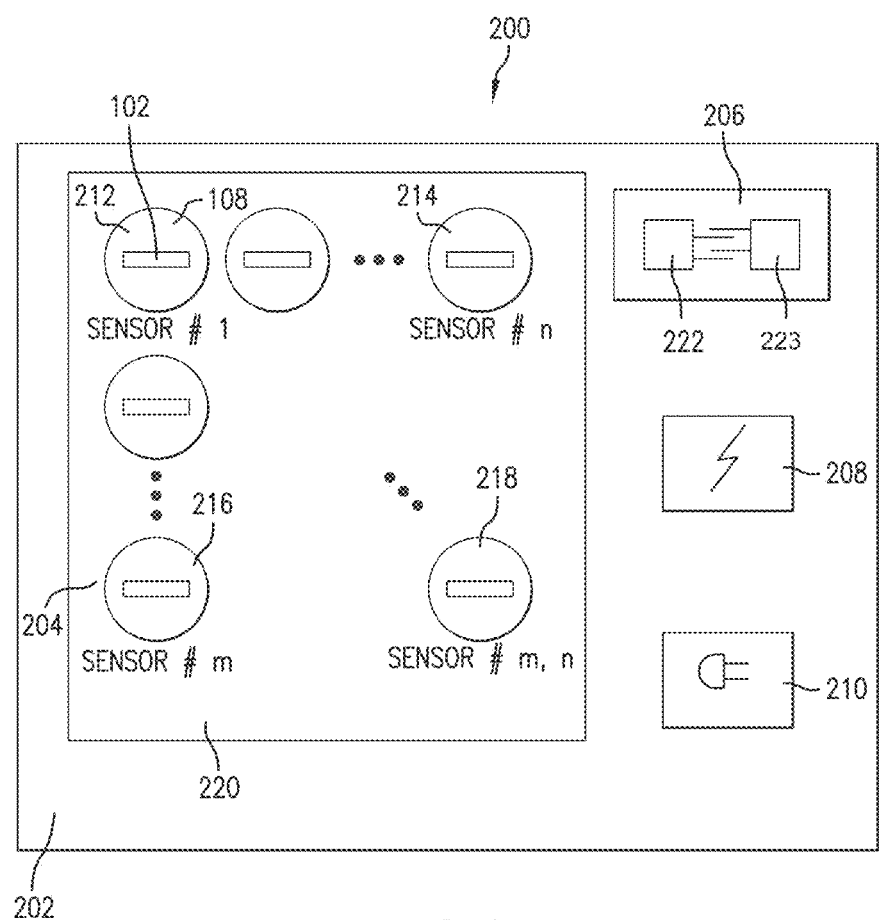
FIG. 2 illustrates an integrated sensor module according to an exemplary embodiment of the present invention.

Hardware components of the disclosed invention are further illustrated in FIG. 2 wherein modular sensors are integrated on a single chip or electronic board 202 (e.g. PCB) thus forming an integrated sensor module 200. Integrated sensor module 200 collects radiation data and is configured to ultimately transmit the data to a remote location such as a wireless base station or other wireless communications device. The integrated sensor module 200 is designed to be an independent sensor system that can be incorporated into many different form factor devices. The small size and self-contained nature of the integrated sensor module 200 to be integrated into a wide range of devices such as a badge, nametag, key chain, bracelet, wrist watch, portable electronic device, MP3 Player, pager, cell phone, smartphone, laptop, tablet, glasses, article of clothing, wallet, purse or jewelry.

The primary sensor array 220 can either be a single sensor, a linear array of sensors, or a matrix of sensors to form the primary or modular sensor array 204, for example employed from the sensor array 100 of FIG. 1. Thus the modular sensor array 204 may utilize only a first sensor #1 (212). Alternatively, modular sensor array 204 may comprise n number of rows such as from first sensor #1 (212) to sensor #n (214). Alternatively and/or in addition, modular sensor array 204 may include m number of columns such as from first sensor #1 (212) to sensor #m (216). Thus, having n number of rows and m number of columns, modular sensor array 204 would extend from first sensor #1 (212) to sensor #m, n (218).

While ionizing radiation sensors 102 encapsulated within "filtration bubbles" 108 are shown for illustrative purposes, those skilled in the art will readily appreciate that the primary sensor array 220 may consist of other suitable types of sensors (e.g., for non-ionizing radiation, hazardous chemicals, or other biochemical substances). Alternative embodiments of the disclosed invention may also include chemical or other sensors in addition and/or as an alternative to ionizing radiation sensor 102. The present invention describes an integrated sensor module 200 that provides unique information about the location and the motion of the sensor when a measurement is obtained. The modular nature of the described platform and device enables the use of other individual sensors or as variable combination of sensors chosen to meet the needs of potential end users. The modularity is achieved by developing the measurement devices as interchangeable modules that can be coupled to a central processing unit (CPU) that handles the collection of time, motion, position and temperature and the communication.

The primary sensor array 220 may be integrated with a motion and global position sensor package The motion and global position sensor package 206 will consist of a single 3-axis MEMS based accelerometer 222 that will determine if a primary data exposure occurs while the device is stationary or in motion as measured on a continual basis. A primary data exposure is a radiological event recorded by the primary sensor array 220. The motion and global position sensor package 206 will consist of a global positioning system (GPS) radio 223 that will determine its position by either the on-board GPS radio 223 and/or by a connected wireless-enabled mobile device (e.g., smartphone or tablet with GPS sensing capability, etc.) or by estimation through a mesh of networked devices. To minimize power consumption of the primary power source the device will preferentially determine location through GPS sensors with the lowest power means available to it. First by the connected wireless-enabled mobile device with GPS capability, second by onboard GPS sensor and third by estimation through a mesh of networked devices.

Although one type of motion and global position sensor package is show in the integrated modular sensor of FIG. 2, other types of motion and global position sensor packages may be used in the present invention. For example, the motion and global position sensor package may include additional types of motion sensors in addition to or instead of an accelerometer.

A wireless system on a chip (SOC) module 208 is configured to integrated sensor module 200. The wireless SOC module 208 is an integrated package consisting of a central processing unit and the wireless transceiver. Combining the wireless transceiver into the CPU chip in a SOC configuration allows a reduction in footprint and energy consumption. The wireless SOC module 208 permits wireless transmission from integrated sensor module 200, for example, to a wireless receiver of another electronic device for electronic communication purpose(s). Such communications ability facilitates efforts, for example, in determining whether integrated sensor module 200 is within range of the aforementioned electronic device as further discussed below.

The power harvester 210 will consist of one or more energy harvesting devices. A power harvester 210 is incorporated into the integrated sensor module 200 and connected to the battery. Power harvester 210 collects energy via motion and/or movement of the integrated sensor module 200 and the ambient light to recharge the battery that supplies power to electronic board 202. Thus, the present invention will actively consume power as it operates and actively communicates to external wireless enabled devices. Power harvester 210 leverages existing work within the MEMS devices to convert periodic (resonant) vibrational mechanical motion into electrical energy to extend the battery that powers the runtime of the radiation measurement sensor capability of the integrated sensor module 200.

Through extensive historical data on the dose levels of personal monitoring radiation detectors it has been determined that 95% of users receive normal occupational level doses. By optionally collecting motion and position only when the detected exposure exceeds a preset threshold. The power consumption of the device can be greatly reduced. The combination of primary exposure data, time, motion and location creates a unique data set which may provide information about the location of radiation fields and the motion of the users through those fields.

Embodiments of the disclosed invention enable the use of ultra-low-power wireless transmission to transmit measured sensor readings from integrated sensor module 200 to a wireless-enabled mobile device (e.g., a smartphone or tablet device, etc.), and the transmission of this information over a wired or wireless data network to an Internet-based server.

The uniquely configured electronic modular configuration of the disclosed invention provides several advantages. The filter material is machine pressed into a spherical shape, and the resulting "filtration bubble" 110 is mechanically pressed into the circuit board containing the ionizing radiation sensor elements 102. Disclosed embodiments of the invention will enact a unique software algorithm (as detailed below) to enable the discrimination between different types of ionizing radiation and different radiation energies. This enables a unique customization of the energy discrimination filtration scheme to improve the accuracy and energy resolution of ionizing radiation measurements using a passive radiation detector.

Radiation attenuating materials 108 are used to modify the response of non-tissue equivalent sensors to allow varying responses to a wide range of radiation qualities. The modified response can then be used by an algorithm to derive the tissue equivalent dose. Currently macro-filters utilized in convention sensor devices have several shortcomings that limit the effectiveness of algorithms by introducing uncontrolled variances. The use of MEMS and nanotechnology manufacturing process to encapsulate the radiation sensors with "filtration bubble" 110 provides several advantages over the traditional macro-filters that will help eliminate the uncontrolled variances. The use of precise MEMS and nanotechnology manufacturing processes allows for the elimination of macro scale variances in the separation of the filter, thickness of the filter and location of the filter. The filtration bubble 110 will eliminate macro scale issues with angular dependence of the filtration. The filtration bubble 110 will also provide a protective layer over the sensitive and possibly fragile sensor 102. The use of multiple attenuating materials 108 around multiple sensors 102 with the use of a software algorithm will allow increased levels of fine discrimination between types of ionizing radiation and radiation energy.

Additional advantages of the described embodiments of the present invention utilize MEMS and nanotechnology sensors to simultaneously detect radiation and other exposure, temperature, time, motion and global position, in combination with an employed software algorithm to correlate exposure levels. Detection occurs with the time, motion and global position of the integrated sensor module 200 wherein the integrated sensor module 200 provides unique and valuable information on how the exposure occurred. The use of modular exposure sensors enables the detection and analysis of exposure to a wide range of phenomena including, for example, radiological, chemical, biological and electromagnetic sources of exposure. The use of time, motion and position further enables the determination of whether the integrated sensor module 200 was moving during an exposure event (e.g., static versus dynamic exposures), and when and where the exposure occurred. The present invention replaces the computationally intensive and time-consuming post-processing and analysis that is currently used by convention sensor devices to determine static versus dynamic exposures. The present invention also provides new time, position and other information that may be used to accurately characterize the source and nature of the exposure. This capability may be particularly important/useful in occupational dosimetry. The inclusion of a temperature sensor is disclosed embodiments enables correction of measurements for temperature-based variance.

Figure 3:
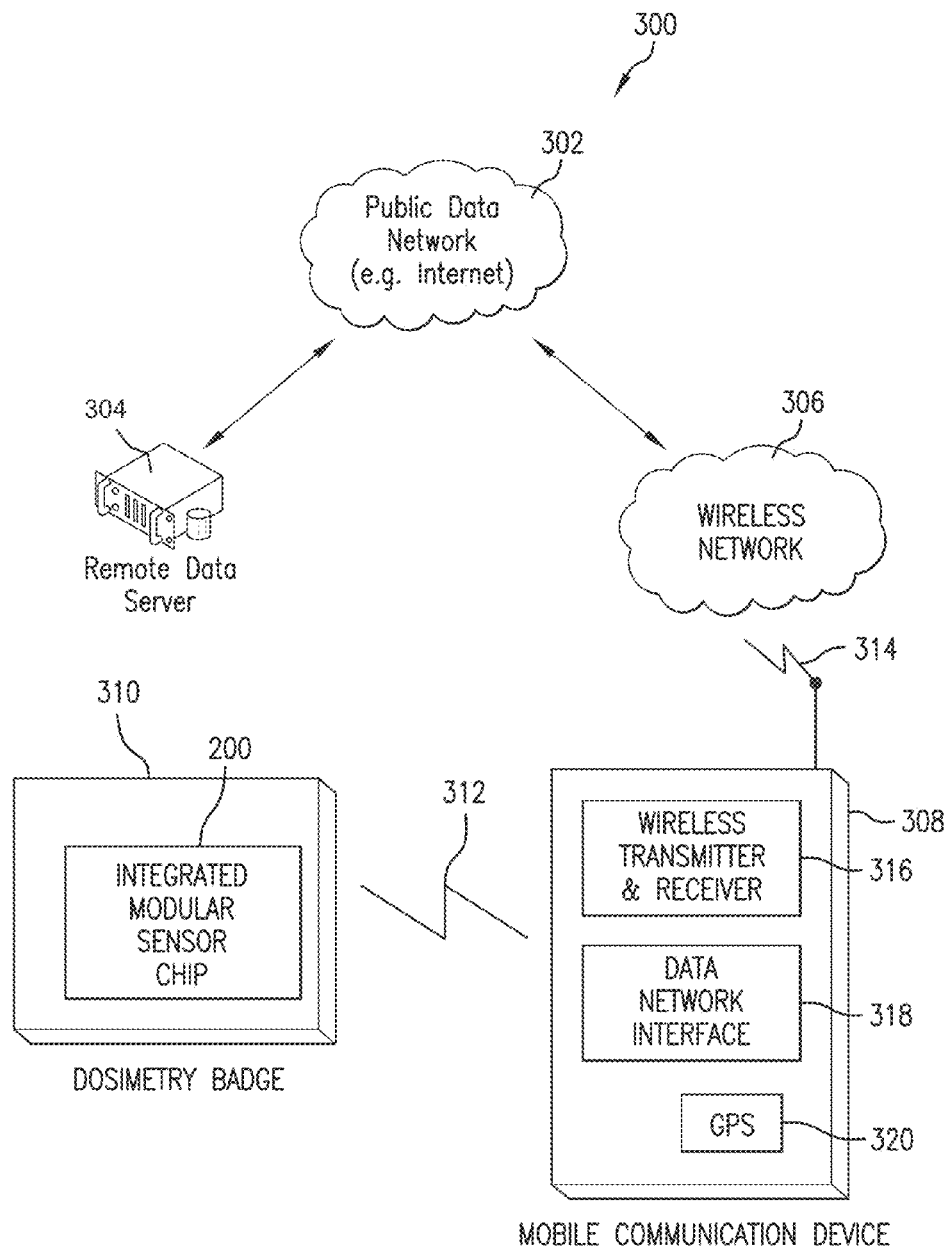
FIG. 3 illustrates a remote sensor network according to an exemplary embodiment of the present invention.

Furthermore, the present invention expands the capabilities and application of traditional, standalone dosimeters by allowing collected data to be transmitted to a central location for processing and redistribution as shown in FIG. 3. FIG. 3 illustrates a remote sensor network 300 according to an exemplary embodiment of the invention. Integrated sensor module 200 is integrated into a dosimetry badge 310. Dosimetry badge 310 is illustrated as a package, for example, including the disclosed electronics packaging including integrated sensor module 200, batteries and a cover of the present invention. Integrated sensor module 200 collects radiation data and ultimately transmits the data to a remote location such as a wireless base station or other wireless communications device such as mobile communications device 308. A remote sensor chip of integrated sensor module 200 may be utilized to transmit the data. In this case, the data may be transmitted via an unspecified wireless transmission communication protocol 312 such as Bluetooth®, ZigBee, ANT, or other standard Wi-Fi protocol, etc.

Examples of mobile communication device 308 may include, for example, a smartphone, tablet or a mobile hotspot, or it might be a non-mobile network device such as a dedicated base station. Mobile communication device 308 may be configured to include a wireless transmitter and receiver 316, data network interface 318, and GPS 320. Wireless SOC module 208 of integrated sensor module 200 is configured to communicate with wireless transmitter and receiver 316. The wireless transmitter and receiver may be a low powered wireless network interface for the mobile communication device 308. The network interface allows the mobile communication device 308 to communicate with SOC module 208 to download collected data. The aforementioned communication facilitates the determination of whether mobile communication device 308 is in range of integrated sensor module 200.

Mobile communication device 308 may also be configured to include a data network interface 318. The data network interface 318 allows mobile communication device 308 to communicate to another wide area wireless network 306 such as via data network transmission communication protocol 314. Examples of data network transmission communication protocol 314 may include Wifi, GSM/EDGE, CDMA, UTMS/HSPA+, LTE or other high speed wireless data communication network. Thus, in an exemplary embodiment, Bluetooth® may be employed to communicate between the dosimetry badge 310 and mobile communication device 308 (such as via wireless transmission communication protocol 312), and the use of LTE to communicate between mobile communication device 308 and wireless network 306 (such as via data network transmission communication protocol 314) of a remote facility such as a hospital or laboratory. In this example, the local network may be represented by wireless network 306 and the public network may be indicated by as public data network 302. By communicating, for example, over the public data network 302, the aforementioned remote facility, such as a hospital or laboratory, may reach, access and/or process information deposited on distributed data server 804.

GPS 320 enables mobile communication device 308 to determine the position of the radiological event. The GPS 320 radio in the mobile communication device 308 provides an alternative means of the determining the position of the integrated sensor module 200. If the integrated sensor module 200 has been paired with a mobile communication device 308, it will preferentially use GPS sensor 320 to determine location to minimize its own power consumption.

Wireless network 306 is configured to communicate with the public data network (e.g., the Internet) 302. A remote data server 304 is configured to communicate with a public data network (e.g., the Internet) 302.

With an electronic data transmission link formed between mobile communication device 308 and remote data server 304, integrated sensor module 200 is capable of transmitting measured data such as to an ultra-low-power wireless-enabled mobile communication device 308 (e.g., a smartphone, tablet or other mobile or non-mobile network device) to leverage the mobile device's existing data or cellular network to communicate collected information to a central web server and, optionally, to use the mobile communication device GPS, or to process the collected data using the mobile communication device CPU. Currently, standalone sensor devices have limited power capacity that must be conserved as much as possible in order to extend battery life. Ultra-low-power wireless communication minimizes the power consumption of device for regular updates. Furthermore, typical data or cellular communication antennas can consume significant power, so utilizing an external mobile communication device also limits the complexity of radiation sensor.

Thus, the use of ultra-low-power wireless transmission capability of the present invention allows transmission of measured sensor readings from integrated sensor module 200 to a wireless-enabled mobile device 308 (e.g., a smartphone or tablet device, etc.), and the transmission of this information over a wireless data network 306 to an Internet-based server 302. This enables the analysis and reporting of measured doses for individual detectors employing integrated sensor module 200 without having to physically send the detector itself to a central location for reading and analysis. The reduces costs and valuable time for receiving data and performing critical analysis. Embodiments of the present invention also allow for multiple systems to receive a plurality of measured doses from a plurality of detectors having integrated sensor module 200. The collection of sensor data from multiple systems enables the analysis and visualization and geographic-based mapping of exposure sources and related population-based trends over time. The connection to the Internet also enables the remote update and troubleshooting of the device.

Disclosed embodiments of the present invention may include mounting the integrated sensor module 200, for example, on multiple, low-cost, semi-autonomous unmanned airborne vehicles (UAV's) such as low-power RF helicopters. A flocking-algorithm may be employed to cause the "flock" of devices to track the position and distribution of airborne radiation, chemicals or other phenomena while remaining in the flock and where the distribution of the flock would correlate with the distribution of the airborne material being tracked.

Figure 4:
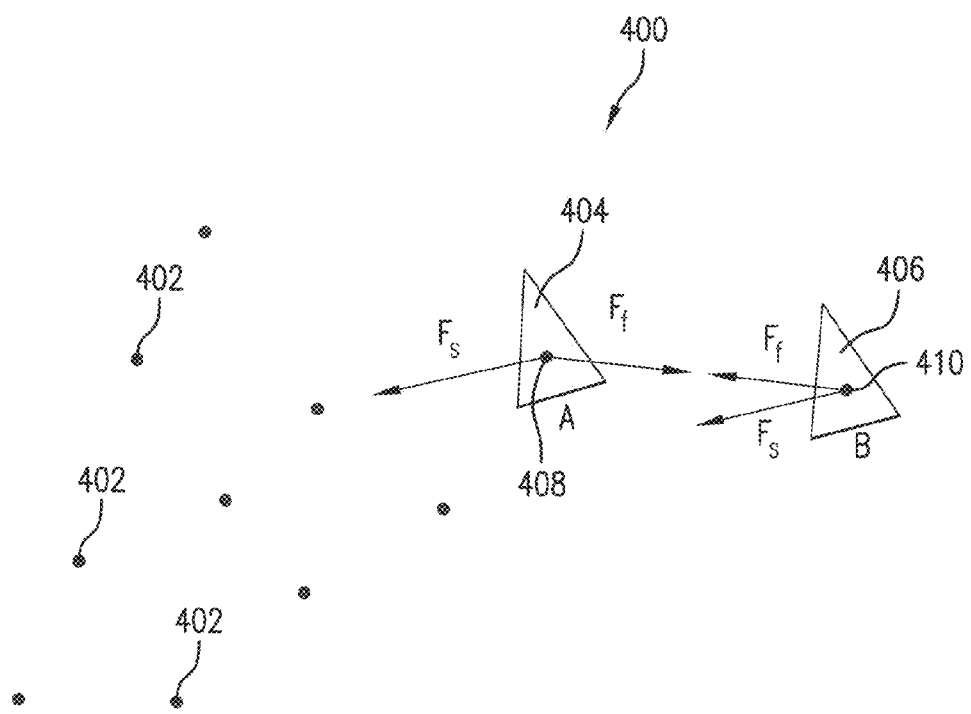
FIG. 4 illustrates an autonomous mobile sensor (AMS) network according to an exemplary embodiment of the present invention.

Thus, in select embodiments, the disclosed invention enables the integration of the integrated sensor module 200 into a mobile platform that may consist of multiple semi-autonomous UAV's to track the position and distribution of airborne materials (radiation, chemicals, biological agents, electromagnetic fields, etc.). The UAV-integrated sensors may utilize flocking algorithms to coordinate between multiple UAV's and track the position and distribution of airborne particles. Turning to FIG. 4 an exemplary autonomous mobile sensor (AMS) network 400 is illustrated. As shown in FIG. 4, the airborne (or waterborne) particles 402 will tend to cluster and then distribute depending, for example, upon prevailing weather patterns. Autonomous mobile sensors (AMS) 404, 406 are shown tracking respective distributed target particles 408, 410. The flocking algorithm will update the position of all UAVs 404, 406 by using a Sensor Force, Fs, proportional to the measurement from the modular sensor array 204 on the UAV, and a Flocking Force, Ff, proportional to the distance to nearby UAV's, to continually optimize the positions of the UAV sensors 404, 406 and to best track the position of the target particles 408, 410. As a result, the distribution of the flock will also correlate with the distribution of the airborne material being tracked.

In another embodiment the disclosed invention may include mounting integrated sensor module 200 on multiple, low-cost, semi-autonomous and unmanned water-based vehicles and tracking, for example, waterborne particles. Again, the use of the previously described flocking-algorithm may be employed to coordinate between multiple unmanned water-based vehicles and to track the position and distribution of any water-based radiation, chemicals or other phenomena.

Advantages of the disclosed invention provide the first use of MEMS and nanotechnology to create a passive integrating electronic ionizing radiation detector with active readout capability and with motion-sensing and position-sensing capabilities and wireless transmission of the sensor readings. Current active dosimeters require continuous power in order to measure dose. Additionally, current passive dosimeters do not provide immediate access to recorded dose measurements. Furthermore, the active readout of a passive radiation sensor disclosed by the present invention provides immediate access to dose information while preserving dose information in the event of power loss. In addition, the present invention describes an electronic platform for recording motion, temperature and position with modular environmental sensors for comprehensive personal and environmental monitoring.

An exemplary integrated sensor module logic flow 500 for integrated sensor module 200 is represented in FIG. 5. A command 502 for reading the sensor is executed. Command 502 includes pre-reading a high-sensitivity sensor 504 to determine if there is a new threshold dose 506 on the sensor.

In determining whether there is a new threshold dose 506 on the sensor, the sensor is enabled to continuously accumulate dose values. When a read is performed on a specially-designated high-sensitivity sensor (referred to hereinafter as a "pre-read" of the dosimeter), then a cumulative value is generated. The previous dose value is subtracted from the cumulative value generated from the pre-read to generate a delta (Δ) value. If the delta (Δ) value above a prescribed dose threshold, then a trigger measurement is taken in step 508. If the delta (Δ) value is not above the prescribed dose threshold then a loopback function is performed to take continuous measurements at a timed interval to read the sensor 502. Described embodiments continuously loop back to pre-read high-sensitivity sensor 504 until a delta (Δ) dose value is detected to be higher than the prescribed dose threshold value. Once a delta (Δ) dose value is detected to be higher than the prescribed dose threshold value, a trigger measurement 508 is enabled to simultaneously read a solid-state sensor array 510 (also see FIG. 6) and read-out of the event data or position of exposure in time 512 (also see FIG. 7).

One disclosed embodiment of the sensor readout logic flow diagram is illustrated in FIG. 6. The solid-state sensor array read-out 600 is the component of the disclosed invention that reads the entire sensor array. A reading from the high-sensitivity sensor indicates that the minimum incremental dose threshold has been reached. The high-sensitivity sensor is solely intended to indicate when the threshold dose has been exceeded. Once the threshold dose has been exceeded, then all of the sensors will be read from a 1-D array, a 2-D array or a 3-D matrix. A 1-D array may just be a row of sensors. A 2-D array may be a table of sensors or a matrix of sensors. A 3-D array would be if you stack up multiple 2-D arrays. There are multiple ways of reading the measurements from the sensors. We could either read each sensor individually 602, or we might read-out along an entire row or column of sensors 604, or we might sum up the output from all of the sensors 606, or we might readout a custom configuration (e.g., four of the sensors in each quadrant if there was an array of multiple sensors (e.g., sixteen sensors). Hence, disclosed embodiments of the described invention provide multiple ways of reading a solid-state sensor array.

One disclosed embodiment of the sensor readout logic flow diagram is illustrated in FIG. 6. The solid-state sensor array read-out 600 is the component of the disclosed invention that reads the entire sensor array. In one example, the high sensitivity sensor may be affixed to a badge. In an event where the badge is exposed to ionizing radiation the disclosed invention can read-out all of the sensors required to calculate the exposed dose. Disclosed embodiments provide the ability to read individual, a whole array of sensors, and a custom configuration of sensors. Accordingly, for various configurations of sensors, the invention may generate readings, for example, for individual sensors 602 such as a one-dimensional array including, for example, a row of sensors. In addition to, or alternatively, dimensional arrays of sensors may be read by disclosed embodiments to include, for example, a table of sensors or a matrix of sensors. Such embodiments of sensor configurations may include a two-dimensional array of sensors including, for example, one or more rows or one or more columns of sensors. Disclosed embodiments may also provide a three-dimensional array, for example, including one or more two-dimensional arrays stacked upon one another. Thus, disclosed embodiments may either read sensors individually 602, perform a two-dimensional read-out, for example, along an entire row or column of sensors 604, or perform a sum of all of the output from all of the sensors 606, or perform a readout for a custom configuration of sensors (e.g., four of the sensors in each quadrant if there was an array of multiple sensors (e.g., sixteen sensors)). Hence, disclosed embodiments of the described invention provide multiple ways of reading a solid-state sensor array.

Disclosed embodiments provide electronic sensing circuitry to generate an analog measurement. The analog measurement is preferably converted to a digital measurement utilizing standard analog to digital conversion circuitry 610. From the digital data, the dose 612 is calculated by implementing an algorithm of the disclosed invention for calculating the dose on a system on a chip (SOC) (e.g., via an arm processor). The calculated dose value is then recorded on a data record 614 which may essentially generate a log of all of the readings on an ongoing basis.

In parallel with the solid-state sensor array read-out 600 of FIG. 6, the disclosed invention executes a read-out of the event data or position of exposure in time 512. The position of exposure read-out logic flow 700 is illustrated in FIG. 7 and may be executed via parallel circuitry. An on-board MEMS accelerometer device 702 is read to determine if the sensor is in motion. Next, the location (which can be considered the position in space with a specified level of granularity or spatial resolution) of the sensor is estimated at step 704. This may be accomplished, for example, by reading the GPS sensor on the integrated sensor module, or by using wireless communication to obtain the location from external location beacons, or by using an on-board algorithm to estimate the location (e.g., using a "dead-reckoning" algorithm), or by communicating with a mobile device (e.g., cell phone) in which the GPS function of the mobile device is utilized to determine the geospatial position, or by estimating the location by triangulation between external location beacons or other dosimeters.

In one embodiment of the present invention using GPS, the GPS receiver of the mobile device determines position by precisely timing the signals sent by GPS satellites. Each satellite continually transmits messages that include the time the message was transmitted and the satellite position at the time of message transmission. The GPS receiver uses the messages it receives to determine the transit time of each message and computes the distance to each satellite using the speed of light. Each of these distances and satellites' locations define a sphere. The receiver is on the surface of each of these spheres when the distances and the satellites' locations are correct. These distances and satellites' locations are used to compute the location of the receiver using navigation equations. In another embodiment, the position may be estimated by triangulating the position such as from a known wireless hub with which the sensor is communicating. Wireless triangulation is the process of determining a location of a point by measuring signal strength between several nodes of the wireless network. A time stamp is generated at step 706 to record the time at which a measurement was taken. This measure correlates to the motion (e.g., point at which on-board MEMS accelerometer device is read 702) and position (e.g., the estimated position of the sensor at step 704) at the time the sensor was read. The time stamp readings from step 706 may then be exported or recorded to the data log. Thus, the exposure event is captured in the data record 708.

Figure 5:
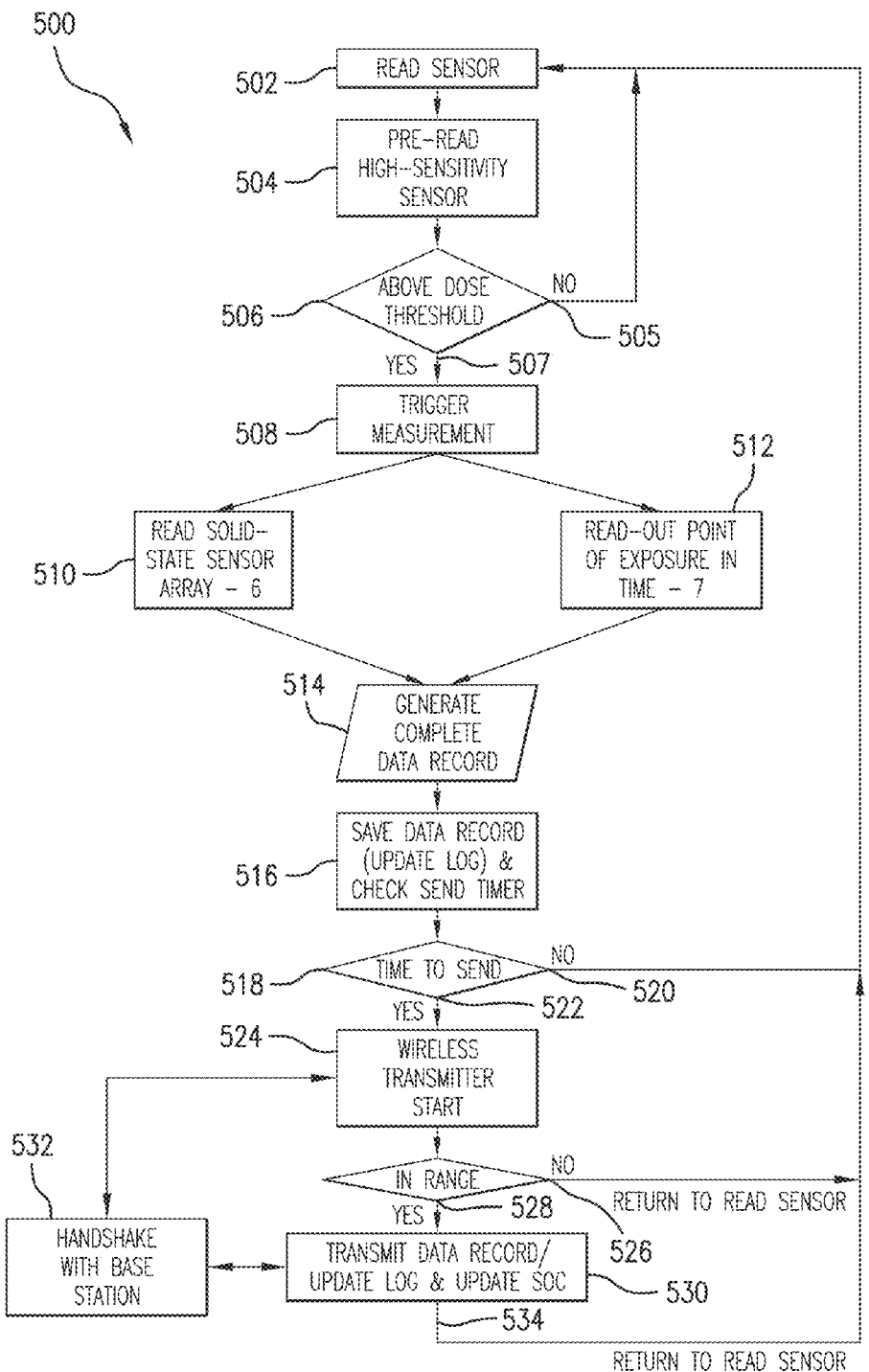
FIG. 5 illustrates an integrated sensor module logic flow according to an exemplary embodiment of the present invention.

Turning again to FIG. 5, the above description outlines the generation of a dose value 510 and a position of exposure in time 512 in the log or recorded data records 614 and 708, respectively, to generate a complete data record 514. The complete data record 514 is saved or updated to the record log and the Send Timer is checked 516. The Send Timer determines when data should be uploaded to the base station 802 or mobile communication device 308 based on a programmable Time To Send value. For example, if the dose exceeds a prescribed threshold value or if the prescribed time has elapsed, then the dose value is transmitted and recorded 522. If the Time to Send value has not been reached, then the device will return to reading 520.

The wireless transmission is started 524 in order to initiate sending a signal from the sensor wireless SOC module 208 of the integrated sensor module 200, for example, to wireless receiver 316 of mobile communication device 308. The sensor's wireless SOC module 208 looks for a handshake response from the wireless transmitter 316 of the mobile communications device 308 to determine if the device is in range for further communication. Wireless SOC module 208 of the integrated sensor module 200 can be configured to communicate with another electronic communications device, such as base station 802, to determine if it is within range of the electronic communications device. If a receiver is within range and a response is received, then the operation continues 528. If a determination is made that the sensor is not in range, then a determination of "no" is made 526 and the operation returns to read the sensor 502 again. When a determination is made that the sensor is in range, a determination of "yes" is made 528, and the data record is transmitted such that the log is updated to show that the data record has been transmitted 530 and to record that the system has been updated. A continuous, never-ending number of readings may occur or as needed in the integrated sensor module logic flow 500.

FIG. 8 illustrates an exemplary embodiment of the disclosed invention in communication with a wireless sensor base station configuration 800. One or more generalized data servers can be connected to a public data network, such as the Internet, to provide an event repository wherein all of the event data is stored in one or more databases accessible over the Internet, and wherein further data analysis can be performed. The Internet is sometimes referred to The Cloud, and access to data over The Cloud for further analysis is sometimes referred to as Cloud Computing.

Figure 6:
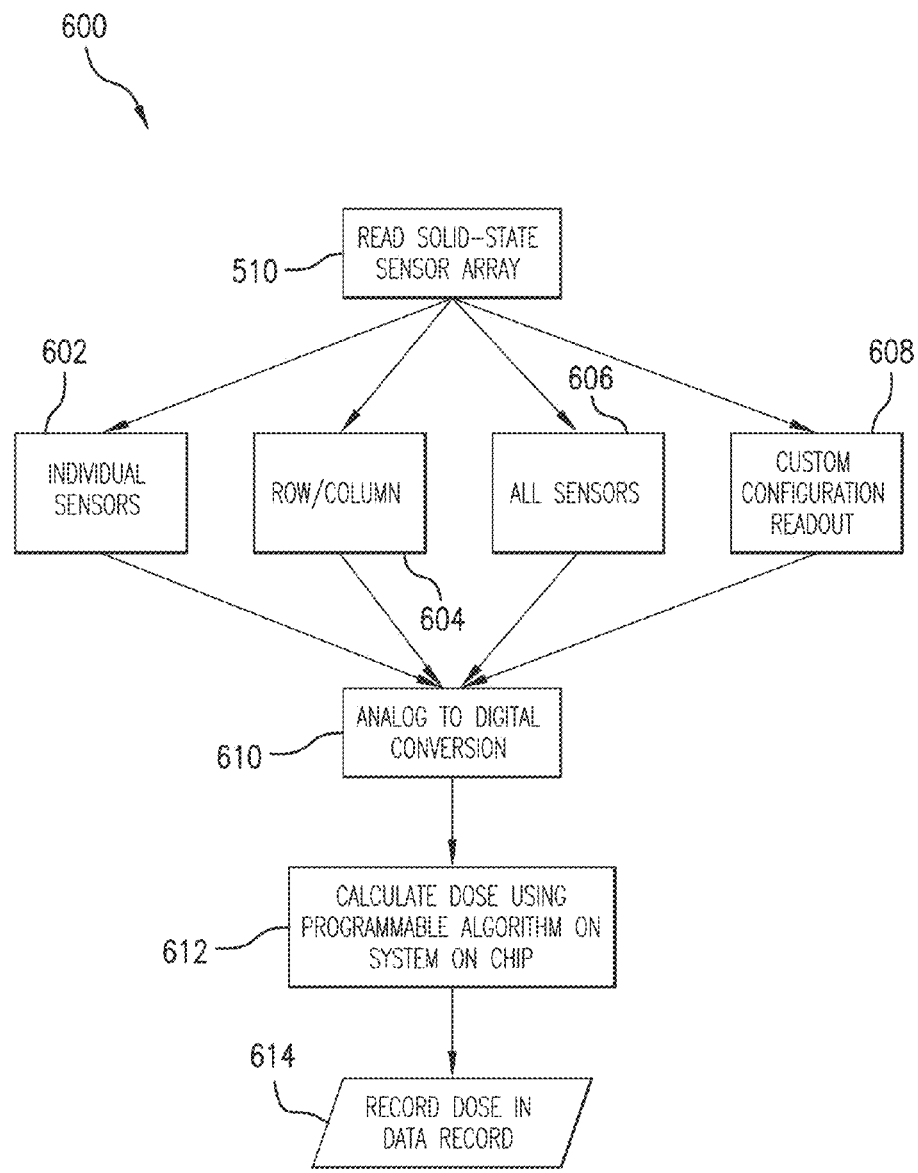
FIG. 6 illustrates a sensor readout logic flow according to an exemplary embodiment of the present invention.
Figure 7:
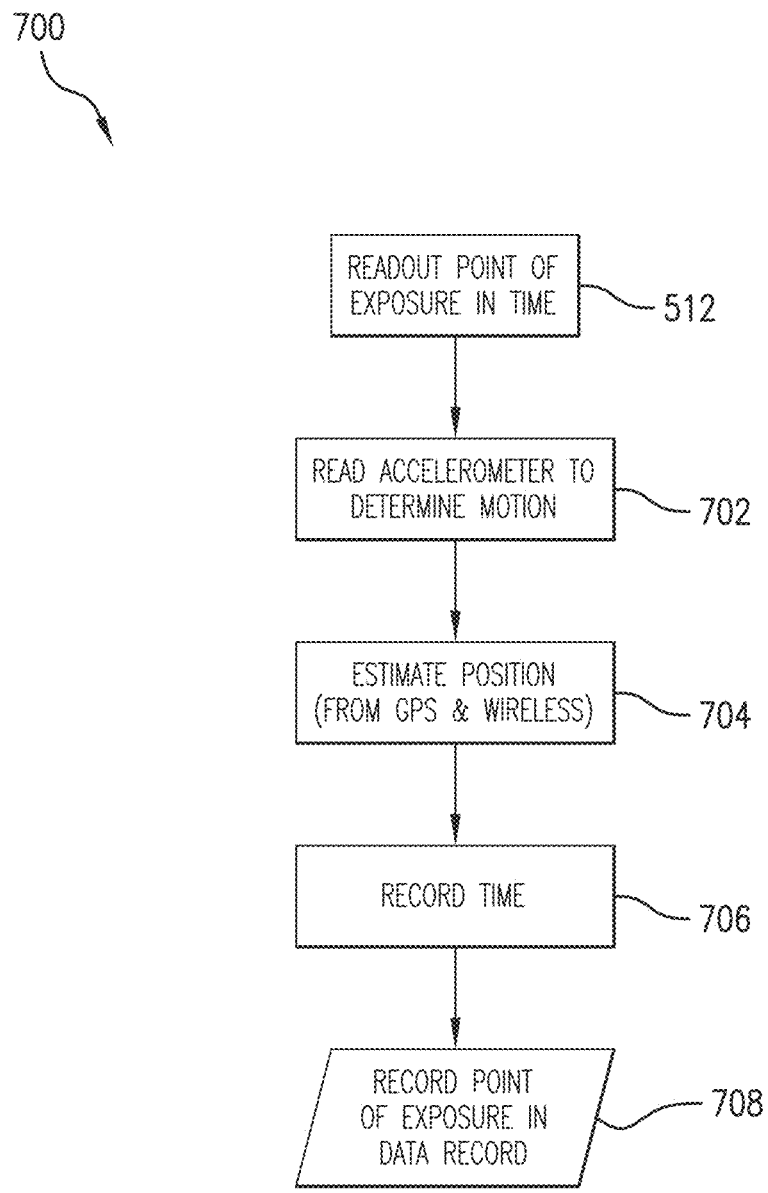
FIG. 7 illustrates a point of exposure readout logic flow according to an exemplary embodiment of the present invention.

Dosimetry badge 310 is illustrated as a package containing, for example, the disclosed electronics packaging including integrated sensor module 200, batteries and a cover of the present invention. Using the algorithm (FIGS. 6 and 7), the integrated sensor module 200 is configured to transmit data to a wireless communications device such as a wireless sensor base station 802. Dosimetry badge 310 may communicate with wireless sensor base station 802 via an unspecified wireless transmission communication protocol including, for example, Bluetooth®, Bluetooth Low Energy (BLE), ZigBee, ANT, ANT+ or other standard wireless communications protocols.

Wireless sensor base station 802 includes a wireless transmitter and receiver 816. Wireless SOC module 208 of integrated sensor module 200 communicates with wireless transmitter and receiver 816 to determine whether base station 802 is in range of integrated sensor module 200 as discussed, for example, in step 532 of FIG. 5 above. Wireless sensor base station 802 may also include a data network interface 818. Data network interface 818 allows wireless sensor base station 802 to communicate to another wireless network such as via data network transmission communication protocol 314. Thus, in an exemplary embodiment, Bluetooth®, Low Energy (BLE) may be employed to communicate between the dosimetry badge 310 and wireless sensor base station 802 (such as via wireless transmission communication protocol 312), and Wi-Fi may be employed to communicate between wireless sensor base station 802 and wireless network 306 (such as via data network transmission communication protocol 314) of a remote facility such as a hospital or laboratory. In this example, the local network may be represented by wireless network 306 and the public network may be indicated by as public data network 302. By communicating, for example, over the public data network 302, the aforementioned remote facility, such as a hospital or laboratory, may reach, access and/or process information deposited on distributed data server 804.

In an optional configuration, wireless sensor base station 802 may include integrated sensor module 200. This configuration enables wireless sensor base station 802 as an event sensing device as well, acting, for example, as an environmental sensor.

As previously discussed, disclosed embodiments of the invention may employ a unique, numerically optimized dose calculation algorithm, running in the embedded system software or, optionally, on the cloud-based server, to enable the discrimination between different types of ionizing radiation and different radiation energies. This enables a unique customization of the energy discrimination filtration scheme to improve the accuracy and energy resolution of ionizing radiation measurements using a passive radiation detector. Disclosed embodiments provide electronic sensing circuitry to generate an analog measurement. The analog measurement is preferably converted to a digital measure utilizing standard analog to digital conversion circuitry 610. From the digital data, the dose 612 is calculated by implementing the algorithm of the disclosed invention for calculating the dose on a system on a chip (SOC) (e.g., via an arm processor). Select embodiments may employ, for example, a machine readable medium having stored thereon sequences of instructions, which when executed by one or more processors, cause one or more electronic devices to perform a set of operations to perform the aforementioned algorithm. The calculated dose value is then recorded on a data record 614 which may essentially generate a log of all of the readings on a continuous basis.

Accordingly, an embodiment of the invention provides a numerically optimized dose calculation algorithm for accurate and reliable personal dosimetry. Disclosed embodiments provided a computational procedure to generate numerically optimized dose calculation algorithms for personal dosimeters using multiple dosimeter elements (typically two-to-four elements). Current embodiments provide a description of how methods of the present invention transforms dosimeter signals to operational quantities for personal dose equivalents such as Hp(10), Hp(3), and Hp(0.07). Some advantages of the computational procedure of the disclosed invention include the ability to automatically generate a numerically optimized algorithm, the absence of branching or empirical decision points, and fast computation speed.

The accurate and reliable measurement of a personal dose equivalent is a key component of radiation dosimetry programs. The personal dose equivalent is typically measured over a wide range of energies and from different radiation sources, including, for example, x-ray and gamma photons, beta particles and neutrons. In order to accurately estimate the dose from different radiation sources, some personal dosimeters incorporate multiple detector elements, each with varying types of radiation filtration materials, and use a dose calculation algorithm, to calculate the personal dose equivalent from a numerical combination of the responses from each detector element.

One approach to calculate the dose is to use a simple linear combination of detector element responses. Such approaches are straight-forward and easy to implement, but may be highly sensitive to noise and often do not reliably provide an accurate estimate of the dose under realistic conditions. Another approach is to use empirically-determined branching and decision points. According to exemplary embodiments, this approach is relatively easy to implement, and improves performance under some conditions, but the empirical decisions are unique to specific conditions, and often subject to systematic biases. Techniques for applying both linear combination and branching methods to radiation dosimetry have been developed, for example, by N. Stanford (e.g., see N. Stanford, Whole Body Dose Algorithm for the Landauer InLight Next Generation Dosimeter. Algorithm Revision: Next Gen IEC; Sep. 13, 2010 and N. Stanford, Whole Body Dose Algorithm for the Landauer InLight Next Generation Dosimeter, Algorithm Revision: Next Gen NVLAP; Sep. 27, 2010).

The present invention provides MATRIX i.e., a computational procedure to automatically generate a dose calculation algorithm that is numerically optimized for a particular dosimeter type (i.e., a particular combination of dosimeter detector elements and filters). In order to minimize systematic bias the disclosed embodiment, i.e., MATRIX calculates a weighted average from representative data, such that no one irradiation field, detector or ratio of detector signals dominates the resultant dose. The following describes the computational procedure used to generate a numerically-optimized dose calculation algorithm for a personal dosimeter using a matrix of element responses obtained from measurements of that type of dosimeter.

Given a personal dosimeter consisting, for example, of multiple filtered detector elements, the detected signal from each detector element is called the element response, and the array of element responses from a given dosimeter is called the detector's element response pattern. For a given type of dosimeter, the matrix resulting from multiple detector element responses at different but known irradiations is called the element response matrix.

The element response matrix is created by exposing a dosimeter to known irradiations at different angles and to mixtures of individual or multiple sources, and then reading the element responses from each detector element. The element response pattern from an unknown irradiated dosimeter is then compared to the patterns in the element response matrix, and a dose is calculated for each source in the response matrix. The final reported dose is the sum of all the individual source doses weighted by a Source Probability Factor. The Source Probability Factor is a measure of how closely the element response pattern of the unknown dosimeter matches the individual element response pattern of known sources.

The steps in the disclosed embodiment, i.e., MATRIX computational procedure 900 are summarized in Table 1 of FIG. 9, and each computational procedure is described in the corresponding sections below.

In step 902, the dosimeter element responses and the corresponding dosimeter response matrix for that type of dosimeter are input, and then the converted values are calculated. For dosimeters employing optically simulated luminescence (OSL) such as LANDAUER's InLight® dosimeters, the dosimeter element responses correspond to the photomultiplier counts from the InLight® Reader. The converted values are calculated from the PMT counts as shown in Equation 1:

$$ConV_n = \frac{PMT\ Counts_n}{Sensit \times Reader\_Cal\_Factor}$$

The response matrix corresponding to the dosimeter type may be read from computer storage. In one disclosed example, e.g., for LANDAUER InLight® dosimeters, the response matrix contains entries (variables) describing the source, the individual element responses, the deep dose equivalent (DDE) conversion factor, and the standard deviations of the responses.

The response matrix selection may be based on empirically derived rules. In order to achieve optimal performance in a certain application, the range of sources in the response matrix is restricted. This technique may cause a systematic error if radiation conditions occur outside the selected range. An implementation of the disclosed embodiment using selection cuts is described, for example, in Brahim Moreno, LDR-Europe Technical Report on a Hybrid MATRIX-Branching dose calculation algorithm, 2013.

Next a dose calculation may be performed. Given a set of measured converted values, the first step is to calculate G1-4 for each field in the response matrix. Note that the values of G for a given field indicate what the SDE would be if the given field matched the actual incident field to the dosimeter.

The expected value of the SDE for a given field could be taken as the simple average of G over the detector elements. This however would be insufficient due to the fact that for some incident radiation fields, several detectors may have signals with high levels of uncertainty. This turns out to be the case with 85Kr β-rays incident upon detectors with filtration over 0.1 g/cc in density thickness. Because of this field is weakly penetrating, the signals received from the filtered elements are too low relative to the noise level to use them to calculate dose.

A way to calculate dose using only detectors with a good signal is to weight the signal of each detector by a factor inversely proportional to the expected uncertainty and then perform a weighted average over the detectors. The first set is to define the expected uncertainty. Assume that each response matrix entry is determined from data for which the counting statistics were negligible (high dose). This error is a combination of the uncertainties due to the irradiation, reading, handling, and material variability. This combined error is computed as the standard deviation of the data used to generate the response matrix, it is symbolized by $\sigma$.

The expected value of the SDE for field j is given by $\overline{G_j}$. The total uncertainty for the ith detector element and jth radiation field is by symbolized by $\sigma_{ij}$.

$$\overline{G_j} = \frac{\sum_{i=1}^{4} \frac{G_{ij}}{\sigma_{ij}^2}}{\sum_{i=1}^{4} \frac{1}{\sigma_{ij}^2}} \quad (2)$$

A goodness of fit statistic for a single radiation field, j, is given in Equation 3.

$$s_j = \sqrt{\sum_{i=1}^{4} \left(\frac{G_{ij} - \overline{G_j}}{\sigma_{ij}\overline{G_j}}\right)^2} \quad (3)$$

The weighting factor for field j is given in Equation 4.

$$W_j = \frac{1}{(e^{s_j} - 1)^2} \quad (4)$$

Now that a weighting factor has been assigned to each field in the response matrix, the reported SDE value, Grep, is calculated. This is done by taking the weighted sum of the expected values for each radiation field $\overline{G_j}$, over the entire response matrix. This is given in Equation 5, where the sum is performed over a response matrix of N fields.

$$G_{rep} = \frac{\sum_{j=1}^{N} W_j \overline{G_j}}{\sum_{j=1}^{N} W_j} \quad (5)$$

The quantification of similarity between the response pattern of a measured set of converted values and the fields in the response matrix can be derived using any optimization technique. Equations 3-4 are based on the χ2 minimization. The source specific statistic and weighting factor are an empirical measure of how well the pattern of a set of measured converted values matches the patterns found in the response matrix.

In step 904, a check for error conditions is performed. In this step, common error conditions are checked and, if detected, the appropriate error conditions are set. The dose is not reported if a serious error condition is detected.

In step 906, dose values are calculated for each source in the response matrix. In this step, a weighted value for Hp(0.07) and Hp(10) are calculated for each element to form the response pattern for this dosimeter. Then a goodness of fit statistic is calculated, and then a source weighting factor is determined.

In step 908, disclosed embodiments calculate the total reportable doses. In this step, the weighted values for Hp(0.07) and Hp(10) for each element are summed, then the source weighting factors for each element are summed. The reportable Hp(0.07) and Hp(10) doses are calculated.

In step 910, an estimate of the most likely source of radiation is performed. In this step, the probable contribution of each source in the response matrix is estimated. In the currently disclosed algorithm, the probable contribution of photons and beta particles is estimated.

In step 912, the final (net) dose values are calculated. In this step, the net dose is calculated by subtracting a control dose from the previously calculated dose. Only net doses greater than 1.0 mrem are reported.

In step 914, the net dose values are outputted, e.g., from memory to storage device. In this step, the net dose is assigned to a specific dosimeter using the unique identification value stored in the dosimeter information database. The calculated Net Dose in computer memory is stored in the database (or exported to an external data file if needed. The results can be formatted to allow the generation of dose-of-record customer dose reports as required by local, national or international regulations.

Figure 10:
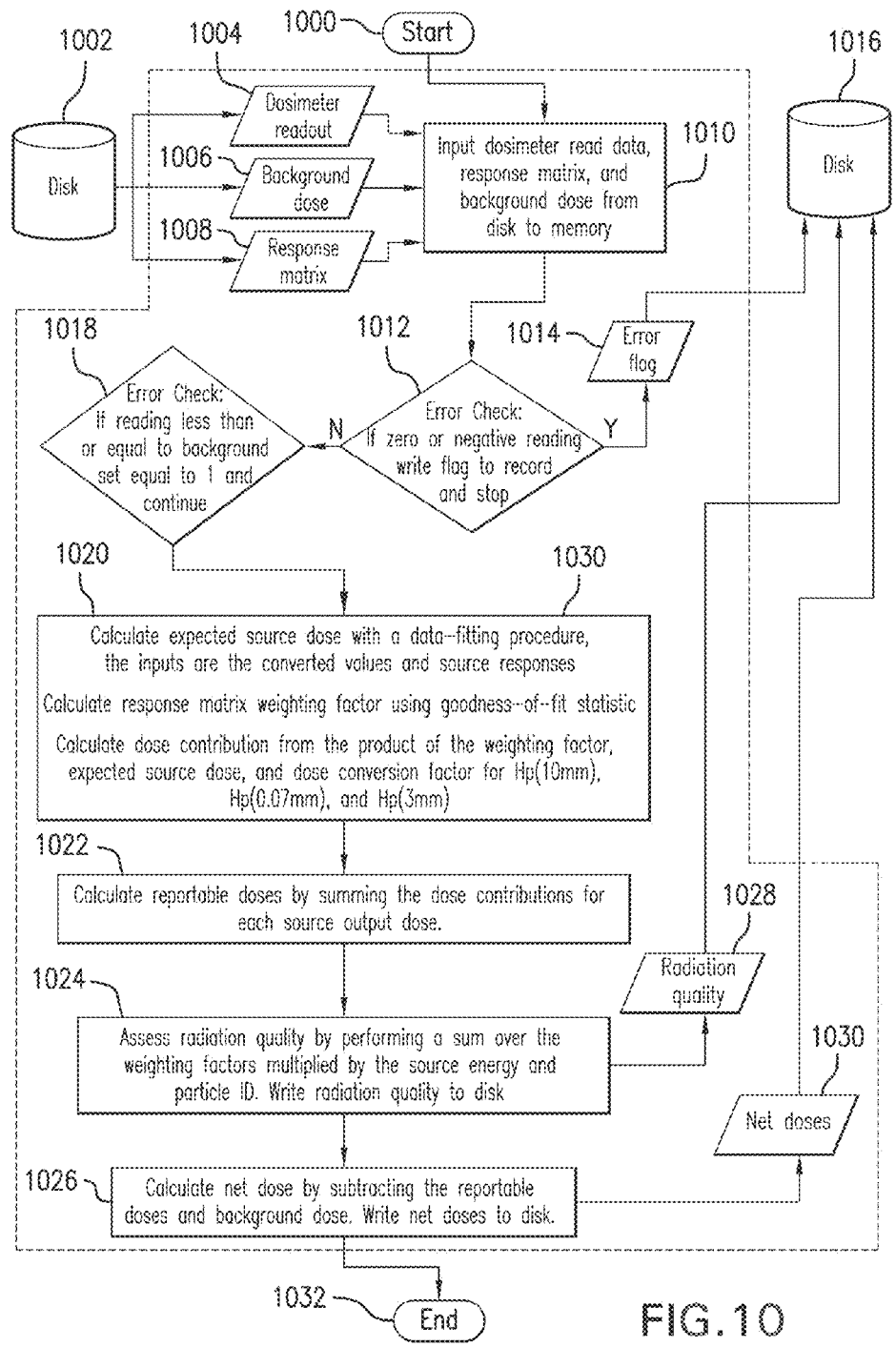
FIG. 10 illustrates a flowchart of the disclosed computational procedure for employing an algorithm according to an exemplary embodiment of the present invention.

A flowchart 1000 of the disclosed computational procedure for employing an algorithm to generate numerically optimized radiation dose calculations for personal dosimeters is illustrated in FIG. 10. Information/data from the dosimeter readout 1004, background radiation dose 1006 and response matrix 1008 may be read and inputted from a computer storage 1002 such as a computer disk and stored to a machine readable medium such as memory 1010. The machine readable medium or memory 1010 may have stored thereon sequences of instructions, which when executed, for example, by one or more processors, may cause one or more electronic devices to perform a set of operations to perform the disclosed computer algorithm. The disclosed computer algorithm processes the raw data (e.g., dosimeter readout 1004, background radiation dose 1006, and response matrix 1008) and transforms it to useful information which may be further written to a computer storage 1016 such as a computer disk where the information may be configured to be displayed as needed.

After the raw data is received to memory 1010, disclosed embodiments check for error conditions 1012. Common error conditions are checked and, if detected, the error may be flagged 1014 and all errors may be tracked/tabulated on computer storage 1016. If there is no error 1018, the raw data is processed by the disclosed computer algorithm 1020. Computer algorithm 1020 begins by applying a mathematical algorithm using prescribed numerical procedures to optimize the response matrix. This may include calculating the expected source dose with a data-fitting procedure. The inputs are the converted values and source responses. The response matrix weighting factor may be calculated using a goodness-of-fit statistic. The weighting factors tell you how much each source contributes to the final dose. An optimization technique may be selected based upon prescribed performance criteria. The Dose contribution may be calculated from the product of the weighting factor, expected source does, and dose conversion factor for personal dose equivalent (e.g., Hp (10 mm), Hp (0.07 mm), and Hp (3 mm)).

Once the optimal fit is found/determined, the reportable doses are calculated 1022 by summing the dose contributions for each source output dose. Radiation quality is assessed 1024 by performing a sum over the weighting factors multiplied by the source energy and particle identification. The radiation quality may be written to computer storage 1028 such as to computer storage 1016. The net dose is calculated by subtracting the reportable doses and background dose. The net doses may be written to computer storage 1030 such as to computer storage 1016.

There is a surge in interest in energy harvesting from human motion due to the rising demand for wearable electronics, such as for patient monitoring in healthcare applications and wearable consumer products[13,14]. However, human vibration and motion energy is generally concentrated below 10 Hz, which may cause difficulty because lower frequency sources are more difficult to design for due to the requirement of either a highly compliant spring or large mass.

The present invention uses energy harvesting through micro mechanical systems (MEMS) and photovoltaic systems to recharge the internal battery and extend the powered lifetime of the integrated sensor module 200. Embodiments of the disclosed invention also extend previous work using the MEMS devices of the integrated sensor module 200 to convert resonant and vibrational mechanical motion into electrical energy and photovoltaic cells to convert ambient lighting into electrical energy. The present invention uses MEMS to convert the random mechanical energy of human motion into electrical energy, and photovoltaics to convert ambient light into electrical energy, both of which can be stored in a battery on the device and later used to power the above-described sensors of the integrated sensor module 200. MEMS based energy harvesting can be accomplished with piezoelectric, electrostatic or magneto-static devices. Disclosed embodiments may detect vibration and motion energy at general concentrations below 10 Hz. Furthermore, disclosed embodiments provide a power harvester, wherein the power harvester converts mechanical vibration energy into electrical energy, and wherein the resonant excitation of the power harvester has a frequency range of approximately 6-8 Hz.

Select embodiments may employ the ability to adjust the energy harvester to maximize the energy collected for a particular application. For example, the aforementioned may include, in a mechanical energy harvesting design, using a magnet and coil, wherein there exists the ability to adjust the size of the coil, size and strength of the magnets, etc. Piezoelectric energy harvesters convert mechanical strain of vibration in electrical energy. Electrostatic energy harvesters collect energy from the changing capacitance of vibrating, separated, charged parallel plate capacitors. Magneto-static energy harvesters collect energy through the motion of a magnet near an electric coil, such that the changing magnetic field of the moving magnet induces current flow in the electric coil. Photovoltaic energy harvesters are based on solar cells that convert solar or ambient indoor light into electric current.

It is well appreciated that other non-limiting embodiments may be employed, for example, conversion of heat (e.g., from a human or animal body or combustive device, or other heat-generating thermocouples) into electrical energy suitable for use in a wireless sensor. Additional embodiments may include conversion of radiofrequency energy into electrical energy suitable for use in a wireless sensor. Other embodiments may employ a radiofrequency receiver coil to optimize the integration of RF receiver coils and sensors, for example, into fabric or clothing materials in order to maximize energy collection and sensing capabilities.

Disclosed embodiments address energy harvesting designs that may be employed as a power source for the disclosed sensor. Recently, magnetically sprung, or levitating, electromagnetic energy harvesters have been studied by researchers[15-23]. One key advantage of magnetic levitation is that the mechanical spring is replaced with a magnetic spring, thus leading to an extended lifetime because the physical spring is the most likely component to fail. Additionally, the removal of a physical spring allows the spring constant to be designed very low, leading to a low resonant frequency. These characteristics make the levitating electromagnetic type energy harvester ideal for human motion energy harvesting.

In another embodiment, U.S. Pat. No. 8,692,206 B2 entitled "Systems, Devices, and Methods Including Implants for Managing Cumulative X-ray Radiation Dosage" issued to Hyde et al. on Apr. 8, 2014 and herein incorporated by reference describes an implantable radiation sensing device including one or more power sources. The implantable radiation sensing device includes a power source including one or more generators configured to harvest mechanical energy from, for example, acoustic waves, mechanical vibration, blood flow, or the like. For example, in an embodiment, the power source includes at least one of a biological-subject (e.g., human)-powered generator, a thermoelectric generator, a piezoelectric generator, an electromechanical generator (e.g., a microelectromechanical system (MEMS) generator, or the like), a biomechanical-energy harvesting generator, or the like. In an embodiment, the power source is electromagnetically, magnetically, acoustically, optically, inductively, electrically, or capacitively coupled, for example, to at least one of the x-ray radiation sensor device, the exposure determination device, a computing device, a transmitter, a receiver, a transceiver, etc.

Non-limiting examples of power sources examples include one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, or the like. Further non-limiting examples of power sources include one or more generators (e.g., electrical generators, thermo energy-to-electrical energy generators, mechanical-energy-to-electrical energy generators, micro-generators, nano-generators, or the like) such as, for example, thermoelectric generators, piezoelectric generators, electromechanical generators, biomechanical-energy harvesting generators, or the like. In an embodiment, the power source includes at least one rechargeable power source. In an embodiment, the power source may include one or more micro-batteries, thin film batteries, fuel cells (e.g., biofuel cells, chemical fuel cells etc.), or the like.

In an embodiment, the implantable radiation sensing device carries the power source. The implantable radiation sensing device may include at least one of a battery, a capacitor, or a mechanical energy store (e.g., a spring, a flywheel, or the like). In an embodiment, the implantable radiation sensing device includes a power source including at least one of a battery, a capacitor, or a rechargeable power or a mechanical energy store. In an embodiment, the power source is configured to manage a duty cycle associated with, for example, detecting and quantifying a transcutaneously received x-ray radiation stimulus, in vivo.

In one embodiment of the present invention, the biological-subject-powered generator is configured to harvest thermal energy generated by the biological subject. In one embodiment, the biological-subject-powered generator is configured to harvest energy generated by the biological subject using at least one of a thermoelectric generator, a piezoelectric generator, an electromechanical generator (e.g., a microelectromechanical system (MEMS) generator, or the like), a biomechanical-energy harvesting generator, or the like. For example, in an embodiment, the biological-subject-powered generator 1136 includes one or more thermoelectric generators configured to convert heat dissipated by the biological subject into electricity. In an embodiment, the biological-subject-powered generator is configured to harvest energy generated by any physical motion or movement (e.g., walking, etc.) by a biological subject. For example, in an embodiment, the biological-subject-powered generator is configured to harvest energy generated by the movement of a joint within the biological subject. In an embodiment, the biological-subject-powered generator is configured to harvest energy generated by the movement of a fluid (e.g., biological fluid) within the biological subject.

In an embodiment, the implantable radiation sensing device includes a transcutaneous energy transfer system. For example, in an embodiment, the implantable radiation sensing device includes one or more power receivers configured to receive power from at least one of an in vivo or an ex vivo power source. In an embodiment, the transcutaneous energy transfer system is electromagnetically, magnetically, acoustically, optically, inductively, electrically, or capacitively coupled to at least one of the x-ray radiation sensor device the exposure determination device, the transmitter, the receiver, the transceiver, or the like. In an embodiment, the transcutaneous energy transfer system is configured to transfer power from at least one of an in vivo or an ex vivo power source to the implantable radiation sensing device.

In an embodiment, the transcutaneous energy transfer system is configured to transfer power to the implantable radiation sensing device and to recharge a power source within the implantable radiation sensing device. In an embodiment, the transcutaneous energy transfer system is electromagnetically, magnetically, acoustically, optically, inductively, electrically, or capacitively coupleable to an in vivo power supply. In an embodiment, the transcutaneous energy transfer system includes at least one electromagnetically coupleable power supply, magnetically coupleable power supply, acoustically coupleable power supply, optically coupleable power supply, inductively coupleable power supply, electrically coupleable power supply, or capacitively coupleable power supply. In an embodiment, the energy transcutaneous transfer system is configured to wirelessly receive power from a remote power supply.

Since on-chip power is often not feasible, the source of power may have to come from, for example, a magnetic field coupling. U.S. Pat. Application Pub. No. US 2010/0219494 A1 entitled "Sub-MM Wireless Ionizing Radiation Detector" by Barnaby published Mar. 2, 2010 and herein incorporated by reference discloses a standard approach implemented in many RFID products[24]. In their 2008 paper, Beyer et al. successfully demonstrated the use of RF energy harvesting to power a MOSFET dosimeter and a bidirectional communication interface[24].

Currently, the majority of autonomous and mobile electronic systems are powered by electrochemical batteries. Although the battery quality has substantially improved over the last two decades, their energy density has not greatly increased. At present, factors such as cost, weight. Limited service time and waste disposal problems (intrinsic to batteries) are impeding the advance in many areas of electronics. The problem is particularly acute in the portable electronics market, where rapidly growing performance and sophistication of mobile electronic devices has led to ever-increasing generating several watts power demands that traditional electrochemical batteries are unable to meet.

U.S. Pat. Application Pub. No. US 2012/0181901 A1 entitled "Method and Apparatus for Mechanical Energy Harvesting Using Planar Microfluidic Device" by Krupenkin et al. published Jul. 19, 2012 and herein incorporated by reference discloses an energy harvester which illustrates a train of energy-producing conductive droplets located along a microscopically thin channel, where droplets are suspended within a liquid dielectric medium and are hydraulically actuated by applying a pressure differential between the ends of channel. Pluralities of separate electrodes 5-1 and 5-2 are disposed along either side of channel, which engage with droplets as they move back and forth within channel during changes in pressure. As conductive droplets move along channel, they create arrays of capacitors with electrodes 5-1 and 5-2, the capacitors changing in stored charge as the droplets move back and worth, generating an electrical current flow. This type of hydraulic activation method provides an important advantage as it allows for efficient direct coupling with a wide range of high power environmental mechanical energy sources, including human locomotion.

While the microfluidic-based energy harvester of Krupenkin et al. exhibits a significant improvement over the state of the art, this actuation method is not well-suited for applications where the energy is being harvested from mechanical vibrations, since the displacement amplitude of a vibration is often too small to initiate motion of droplets along a channel. Yet, such vibrations constitute a readily available source of energy in many important environments, including transportation (e.g., automotive, aerospace, rail), industrial machinery, and the like. Thus, any method that can provide effective actuation of microscopically small liquid droplets by environmental mechanical vibrations would be highly beneficial, as it would allow for the extension of energy harvesting to a broader range of environments, power demands that traditional electrochemical batteries are unable to meet.

One of the technologies that holds great promise to substantially alleviate the current reliance on the electrochemical batteries is high power energy harvesting. The concept of energy harvesting works towards developing self-powered devices that do not require replaceable power supplies. In cases where high mobility and high power output is required, harvesters that convert mechanical energy into electrical energy are particularly promising, inasmuch as they can tap into a variety of "high power density" energy sources that exhibit mechanical vibrations.

High power harvesting of mechanical energy is a long-recognized concept, yet it has not been able to be commercialized, due at least in part to the lack of a viable energy harvesting technology. Existing methods of mechanical-to-electrical energy conversion such as electromagnetic, piezoelectric, or electrostatic do not allow for effective direct coupling to most of the high power environmental mechanical energy sources. Bulky and expensive mechanical or hydraulic transducers are required to convert a broad range of aperiodic forces and displacements typically encountered in nature into a form accessible for conversion using these methods.

Recently, a new approach to energy harvesting has been proposed that substantially alleviates the above-mentioned problems, the new approach being the use of a microfluidics-based energy harvester. In particular, a high power microfluidics-based energy harvester is disclosed in U.S. Pat. No. 7,898,096 entitled "Method and Apparatus for Energy Harvesting Using Micro fluidics" issued to T. N. Krupenkin on Mar. 2, 2011 and herein incorporated by reference.

Krupenkin discloses an apparatus comprising a mechanical-to-electrical energy converting device having a plurality of electrodes and a fluidic body which comprises spatially separated conductive and dielectric liquid regions. The fluidic body is configured to reversibly move as a whole with respect to the plurality of electrodes under the influence of a mechanical force. Each cycle of the reversible motion of said fluidic body causes multiple alternations of the amount of electrical charge accumulated by the electrodes, whereby generating electrical current flow between the electrodes.

The apparatus of Krupenkin comprises two substrates and disposed substantially co-planar and separated by spacers and. Spacers and are disposed in such a way as to form a channel. A plurality of electrodes is disposed on substrate and a plurality of electrodes, is disposed on substrate. Substrates and spacers can be made of any solid dielectric material such as glass, textolite, or a solid plastic, including polycarbonate, polypropylene, or polytetrafluoroethylene. The electrodes can be made of any solid conductive material, such as gold or tantalum, or indium tin oxide glass. In some preferred embodiments comprise a tantalum film or a gold film.

A movable fluidic body is disposed in channel and configured to slide along channel past electrodes. Fluidic body consists of two immiscible liquids, one being a dielectric liquid and the other one being an electrically conductive liquid. Examples of suitable electrically conductive liquids include aqueous salt solutions and molten salts. Exemplary aqueous salt solutions include 0.01 molar solutions of salts such as $CuSO_4$, LiCl, $KNO_3$, or NaCl. Exemplary molten salts include 1-ethyl-3-methylimidazolium tetrafluoroborate and 1-ethyl-3-methylimidazolium trifluoromethanesulfonate, which are both commercially available. In other cases the conductive liquid can comprise liquid metals such as, gallium, indium or mercury. Examples of suitable dielectric liquids include silicone oils and alkanes. Exemplary silicone oils include polydimethylsiloxane and polydiphenylsiloxane, and exemplary alkanes include nonane and heaxadecane.

Conductive and dielectric liquids are spatially separated in a plurality of distinct regions. Dielectric liquid regions and conductive liquid regions are arranged in a periodic alternating pattern, such that conductive and dielectric regions regularly alternate. The boundaries between immiscible liquid regions are preserved by the surface tension forces, giving fluidic body an ability to move as a whole, e.g. slide along channel without disturbing the arrangement and volume of the above-mentioned distinct liquid regions.

The needs remaining in the art are addressed by the present invention, which relates to the harvesting of electrical energy from mechanical, vibrational movement and, more particularly, to the utilization of a plurality of microfluidic elements to convert vibrational energy into useful electrical energy.

In accordance with an exemplary embodiment of the present invention, an array of conductive liquid droplets is disposed on a base substrate and separated from a dielectric-covered electrode by an elastic spacer, forming a capacitive array structure. The elastic spacer is periodically compressed in response to external vibrations, which in turn causes the droplets to be periodically squeezed between the electrode and base substrate. The droplet compression increases the contact area between the droplets and the electrode, creating periodic changes in the amount of electrical charge accumulated between the electrodes, resulting in electrical energy production in the form of a current flowing between the electrodes.

In one case, a proof mass may be attached to the microfluidic energy harvester, where any vibrations impressed upon the proof mass will be translated to the energy harvester and create periodic compression of the elastic spacer and compression of the plurality of conductive droplets. Alternatively, a direct force (period in nature) may be applied to the microfluidic energy harvester to generate electrical energy from the periodic compression of the conductive droplets.

In an alternative embodiment, multiple arrays of elastic spacer and conductor, increasing the amount of energy that is produced for a given surface area (i.e., "footprint'").

In one instance, the present invention can be defined as an apparatus for converting mechanical energy into electrical energy comprising a plurality of electrically conductive liquid droplets disposed in a planar arrangement, a planar electrode disposed in a parallel, spaced-apart relationship with the plurality of electrically conductive liquid droplets, a dielectric layer positioned between the plurality of electrically conductive liquid droplets and the planar electrode so as to form a capacitive structure therewith, an elastic spacer element disposed between the plurality of electrically conductive liquid droplets and the planar electrode so as to surround the plurality of electrically conductive liquid droplets, such that the application of mechanical energy to the apparatus compresses the elastic spacer element and the plurality of electrically conductive liquid droplets, increasing a contact area between said plurality of electrically conductive liquid droplets and the dielectric layer and also an overlap area with the planar electrode, and an electrical circuit means, electrically coupled between the plurality of electrically conductive liquid droplets and the planar electrode so as to apply a bias voltage therebetween and transfer electrical current generated in response to the change in capacitance associated with the change in overlap area to a power consuming element.

The present invention also describes a method of harvesting electrical energy from vibrational motion by disposing a plurality of electrically conductive liquid droplets on a substrate, covering the plurality of electrically conductive liquid droplets with a layer of dielectric material, surrounding the combination of the electrically conductive liquid droplets and layer of dielectric material with an elastic spacer element, positioning a planar electrode over the dielectric material so as to form a capacitive structure with the dielectric material and the plurality of electrically conductive liquid droplets, applying a predetermined bias voltage between the planar electrode and the plurality of electrically conductive liquid droplets, and subjecting the arrangement to a periodic mechanical force so as to compress and then decompress the elastic spacer and the plurality of electrically conductive liquid droplets in a manner to periodically change the capacitive value of the arrangement and create an electrical current output therefrom.

WO 2008/109153 PCT/US2008/003064 entitled "Electrical Energy Generator" by Lemieux published Sep. 12, 2008 and herein incorporated by reference discloses a device for harvesting mechanical energy from a moving mass and converting the harvested mechanical energy into usable electrical energy. The device permits the capture of mechanical energy imparted to the device from movement, such as human gait activities, and the conversion of the captured mechanical energy into electrical energy. The device may be used to provide power to a wide variety of electronic devices.

Mechanical energy comprises a number of forms of energy including, but not limited to kinetic energy. Mechanical energy is manifested in the bodies of humans and animals as a result of their physical processes. Such physical processes include voluntary body movements. Amongst voluntary body movements are gait processes. Gait activities include stepping, walking, running, climbing, jumping, and similar activities. Other voluntary body movements include grasping, reaching, shaking, swinging, stretching, etc. All voluntary body movements are manifested as motion of body members having mass so that all voluntary motor activities develop kinetic energy. Further, voluntary motor activities may impart kinetic energy to peripheral masses engaged with a moving body.

It is often desirable to convert mechanical energy to electrical energy. An example is the conversion of kinetic energy into electrical energy as the kinetic energy of a mass moves a magnetic field relative to a conductive coil thereby converting the kinetic energy of the mass to electrical energy by action of electromagnetic induction.

Kinetic energy is manifested in the bodies of animals and humans, as a result of different voluntary motor activities. Voluntary motor activities include, for example, gait processes, leg movements, arm movements, head movements, torso movements, and the like. Kinetic energy is also manifested in the objects or masses that are moved by a human or animal in the course of transporting them. Some voluntary motor activities, such as human walking gait, are rhythmic activities which have a predictable frequency or periodicity. In the case of human walking gait, the predictable frequency is approximately 2 Hz.

An electrical energy generator for harvesting kinetic energy and converting the harvested kinetic energy developed or imparted by voluntary motor activities into electrical energy is provided. The electrical energy generator may generally comprise a housing, an induction coil, an electromagnetically active mass movable in a reciprocating manner relative to the housing, and at least one spring engaging the electromagnetically active mass to the housing.

According to certain illustrative embodiments, the electrical energy generator generally comprises a housing, an induction coil, an electromagnetically active mass movable in a reciprocating manner relative to the housing, a first spring engaged with the mass and the housing, and a second spring engaged with the mass and the housing.

According to further illustrative embodiments, the electrical energy generator comprises a housing, an induction coil, an electromagnetically active mass movable in a reciprocating manner relative to the housing, a first spring engaged with the mass and the housing, a second spring engaged with the mass and the housing, wherein the electromagnetically active mass is constrained within the housing to minimize or otherwise substantially prevent non-reciprocating movement of the mass.

According to other illustrative embodiments, the electrical energy generator comprises a housing, an induction coil, an electromagnetically active mass movable in a reciprocating manner relative to the housing, a first spring engaged with the mass and the housing, and a second spring engaged with the mass and the housing, and means of mitigating motion retardation of the electromagnetically active mass within the housing.

According to additional illustrative embodiments, the electrical energy generator comprises a housing, an induction coil, an electromagnetically active mass movable in a reciprocating manner relative to the housing, a first spring engaged with the mass and the housing, and a second spring engaged with the mass and the housing, and at least one spring deflection adjustor.

It should be noted that the electrical energy generator may include a combination of two or more of means for constraining the non-reciprocating movement of the electromagnetically active mass within the housing, means for mitigating motion retardation of the electromagnetically active mass within the housing, and at least one spring deflection adjustor.

The device harvests mechanical energy and converts the harvested mechanical energy into electrical energy. By harvesting mechanical energy from the reciprocating mass and converting it into electrical energy, the device acts as a linear electrical generator. The generated electrical energy may be used to power a wide variety of electronic devices including, without limitation, locators, signaling equipment, entertainment equipment, energy storage equipment, radio receivers, radio transmitters, wireless telephones, cameras, global positioning system (GPS) equipment, and like electronic devices.

It is readily appreciated that although examples of dosimetry processing devices are disclosed herein, they may be implemented on any suitable computer system or computing device. It is to be understood that the devices and systems of the examples described herein are for exemplary purposes, as many variations of the specific hardware and software used to implement the examples are possible, as will be appreciated by those skilled in the relevant art(s). Furthermore, the system of the examples may be conveniently implemented using one or more general purpose computer systems, microprocessors, digital signal processors, and micro-controllers, programmed according to the teachings of the examples, as described and illustrated herein, and as will be appreciated by those ordinary skill in the art. The examples may also be embodied as a non-transitory computer readable medium having instructions stored thereon for one or more aspects of the present technology as described and illustrated by way of the examples herein, as described herein, which when executed by a processor, cause the processor to carry out the steps necessary to implement the methods of the examples, as described and illustrated herein.

WO 2008/109153 PCT/US2008/003064 entitled "Event Dosimeter Device and Methods Thereof" by Borkholder et al. published Aug. 30, 2012 and herein incorporated by reference discloses a power system that includes a battery coupled between a regulator and an energy harvester device, although other types of power systems with other types and numbers of components, such as one without an energy harvester and/or without a regulator could be used. In this example, the battery is non-rechargeable and non-user replaceable so the dosimetry apparatus is designed to be disposable by way of example only, although other types of batteries can be used, such as a user-replaceable and rechargeable batteries. With this exemplary disposable design and the associated lower cost, multiple dosimetry apparatuses may be utilized on each person to improve the quality of the collected data and the resulting injury risk assessments. Additionally, with this disposable design for this example of the dosimetry apparatus it is easier to incorporate design changes and update algorithms as the dosimetry apparatus is rolled out for product shipments. As a result, with this exemplary design the latest version always is being delivered out to customers in the field, while traditional (non-disposable) systems would have to somehow incorporate an upgrade. The regulator is coupled to regulate power provided by the battery to the dosimetry processing device. The energy harvester device, such as solar or vibration energy device by way of example only, can be used to supply power to the system and/or recharge the battery, although other types and numbers of energy harvester devices could be used.

An optional wireless location determination system is coupled to the dosimetry processing device to provide location data for the dosimetry apparatus, which can be correlated with and stored with the obtained sensor readings. Examples of location determination systems include a global position system (GPS) or positioning systems based upon triangulation of wireless signals from base stations or other wireless beacons; other types and numbers of location determination systems could also be used.

Thus, in one embodiment, the present invention employs an energy harvester that converts light energy into electrical energy suitable for use in a wireless sensor.

In another embodiment, the present invention employs an energy harvester that converts mechanical vibrational energy into electrical energy suitable for use in a wireless sensor. The mechanical vibrational energy may be due to human motion, the motion of a human limb or other activity by a human. The mechanical vibrational energy may also be caused by the vibrations of a machine or infrastructure on which a wireless sensor is mounted.

In yet another embodiment, the present invention employs an energy harvester that converts light generated by any source such as the sun (solar energy), artificial lighting, a laser beam focused on the device, etc. into energy.

In yet another embodiment, the present invention employs an energy harvester that converts an radiofrequency radiation from RF-emitting sources into energy.

In yet another embodiment, the present invention employs an energy harvester that uses a thermocouple to convert heat from the human body, from a machine, from a combustive device or generated by human motion into electrical energy suitable for use in a wireless sensor.

In still another embodiment, the present invention employs an energy harvester that converts radiofrequency energy into electrical energy suitable for use in a wireless sensor. In some embodiments, a radiofrequency receiver coil of the energy harvester may be adjusted to optimize the harvesting of radiofrequency energy. Integration of the receiver coils and sensors into piece of fabric, such as a piece of clothing, may be done in order to maximize energy collection and sensing capabilities. Furthermore, the radiofrequency receiver may be disclosed, for example, on a printed circuit board (PCB) such as in a holder surrounding a prescribed electrical device such as a dosimeter. In a disclosed embodiment, the size and shape of the radiofrequency receiving antenna may be embedded in the holder and can be adjusted to optimize the collection of RF energy.

In yet another embodiment, the present invention employs an energy harvester that has the ability to be adjusted to maximize the energy collected for a particular application. For example, a mechanical energy harvester using a magnet and coil, depending on the particular application, the size of the coil, the size and strength of the magnets, etc., may be adjusted.

Figure 11:
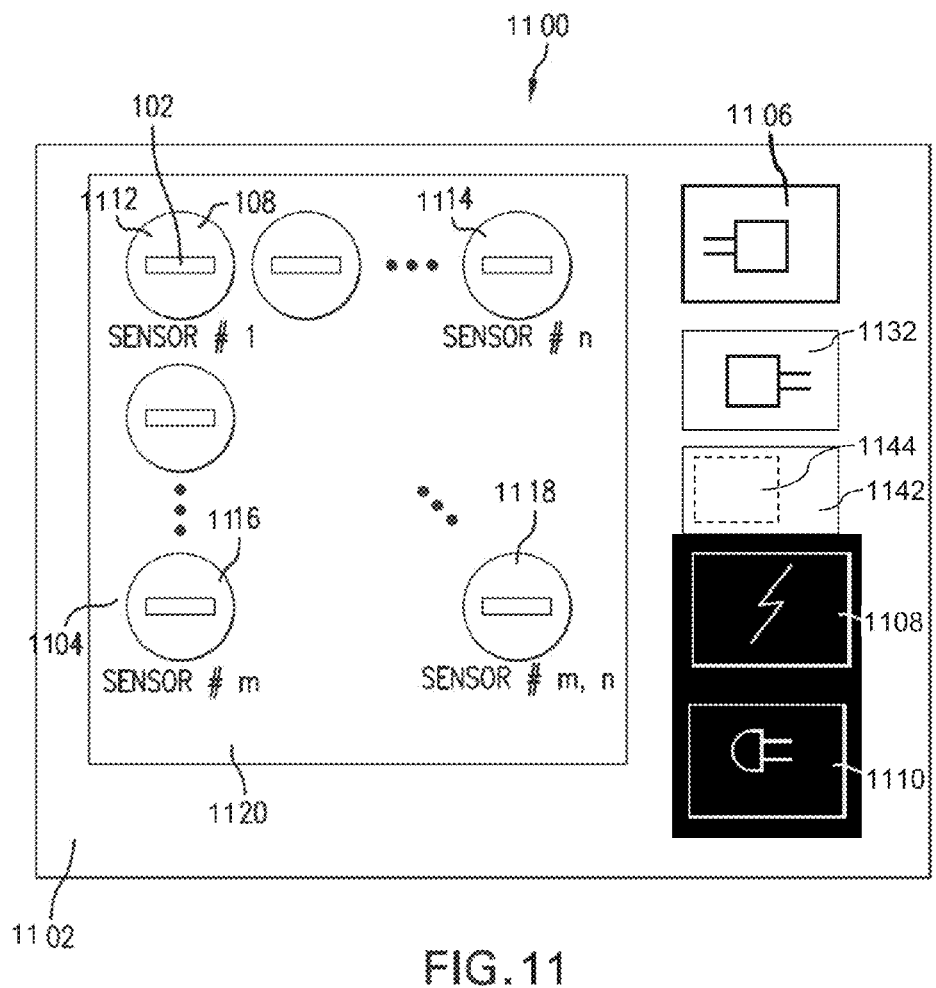
FIG. 11 illustrates an integrated sensor module according to an exemplary embodiment of the present invention.

Hardware components of the disclosed invention are further illustrated in FIG. 11 wherein modular sensors are integrated on a single chip or electronic board 1102 (e.g., PCB) thus forming an integrated sensor module 1100. Integrated sensor module 1100 collects radiation data and is configured to ultimately transmit the data to a remote location such as a wireless base station or other wireless communications device. The integrated sensor module 1100 is designed to be an independent sensor system that can be incorporated into many different form factor devices. The small size and self-contained nature of the integrated sensor module 1100 to be integrated into a wide range of devices such as a badge, nametag, key chain, bracelet, wrist watch, portable electronic device, MP3 Player, pager, cell phone, smartphone, laptop, tablet, glasses, article of clothing, wallet, purse or jewelry.

The primary sensor array 1120 can either be a single sensor, a linear array of sensors, or a matrix of sensors to form the primary or modular sensor array 1104, for example employed from the sensor array 100 of FIG. 1. Thus the modular sensor array 1104 may utilize only a first sensor #1 (1112). Alternatively, modular sensor array 1104 may comprise n number of rows such as from first sensor #1 (1112) to sensor #n (1114). Alternatively and/or in addition, modular sensor array 1104 may include m number of columns such as from first sensor #1 (1112) to sensor #m (1116). Thus, having n number of rows and m number of columns, modular sensor array 1104 would extend from first sensor #1 (1112) to sensor #m, n (1118).

While ionizing radiation sensors 102 encapsulated within "filtration bubbles" 108 are shown for illustrative purposes, those skilled in the art will readily appreciate that the primary sensor array 1120 may consist of other suitable types of sensors (e.g., for non-ionizing radiation, hazardous chemicals, or other biochemical substances). Alternative embodiments of the disclosed invention may also include chemical or other sensors in addition and/or as an alternative to ionizing radiation sensor 102. The present invention describes an integrated sensor module 1100 that provides unique information about the location and the motion of the sensor when a measurement is obtained. The modular nature of the described platform and device enables the use of other individual sensors or as variable combination of sensors chosen to meet the needs of potential end users. The modularity is achieved by developing the measurement devices as interchangeable modules that can be coupled to a central processing unit (CPU) that handles the collection of time, motion, position and temperature and the communication.

The primary sensor array 1120 may be integrated with a global position sensor package 1106. The global position sensor package 1106 comprises a global positioning system (GPS) radio that will determine its position by either the on-board GPS radio and/or by a connected wireless-enabled mobile device (e.g., smartphone or tablet with GPS sensing capability, etc.) or by estimation through a mesh of networked devices. To minimize power consumption of the primary power source the device will preferentially determine location through GPS sensors with the lowest power means available to it. First by the connected wireless-enabled mobile device with GPS capability, second by onboard GPS sensor and third by estimation through a mesh of networked devices. Integrated sensor module 1100 includes one or more motion sensors in motion sensor package 1132. In one embodiment, motion sensor package 1132 includes single 3-axis MEMS based accelerometer that will determine if a primary data exposure occurs while the device is stationary or in motion as measured on a continual basis. A primary data exposure is a radiological event recorded by the primary sensor array 1120. Integrated sensor module 1100 includes a computer 1142 comprising a processor 1144 for processing data from the sensors from modular sensor array 1104, global position sensor package 1106 and motion sensor package 1132.

Computer 1142 may transfer this data wirelessly to second computer (not shown) or other electronic device (not shown) via wireless system on a chip (SOC) module 1108. The second computer or other electronic device may process the data and/or display the data to a user either before or after processing the data. For example, motion data from motion sensor package 1132 may be processed by computer 1142 and wirelessly sent to a second computer or other electronic device. Alternatively, wireless SOC module 1108 may be used to transfer unprocessed data from modular sensor array 1104, global position sensor package 1106 and motion sensor package 1132 to a second computer or other electronic device for additional processing and/or displaying to a user. For example, motion data from motion sensor package 1132 may be wirelessly sent to a second computer or other electronic device, such as the mobile communication device or the remote data server shown in FIG. 3 or the distributed data server shown in FIG. 8, for processing and/or displaying to a user. In addition to motion data, motion sensor package 1132 may also provide to computer 1142 or to the second computer identification data relating to the individual wearing integrated sensor module 1100

A wireless system on a SOC module 1108 is configured to integrated sensor module 1100. The wireless SOC module 1108 is an integrated package consisting of a central processing unit and the wireless transceiver. Combining the wireless transceiver into the CPU chip in a SOC configuration allows a reduction in footprint and energy consumption. The wireless system on a SOC module 1108 permits wireless transmission from integrated sensor module 1100, for example, to a wireless receiver of another electronic device for electronic communication purpose(s). Such communications ability facilitates efforts, for example, in determining whether integrated sensor module 1100 is within range of the aforementioned electronic device as further discussed below.

The power harvester 1110 may include one or more energy harvesting devices. A power harvester 1110 is incorporated into the integrated sensor module 1100 and connected to the battery. Power harvester 1110 collects energy via motion and/or movement of the integrated sensor module 1100 and the ambient light to recharge the battery that supplies power to electronic board 1102. Thus, the present invention will actively consume power as it operates and actively communicates to external wireless enabled devices. Power harvester 1110 leverages existing work within the MEMS devices to convert periodic (resonant) vibrational mechanical motion into electrical energy to extend the battery that powers the runtime of the radiation measurement sensor capability of the integrated sensor module 1100.

U.S. Patent Application No. 2012/0271121 to Della Torre et al. entitled "INTEGRATED BIOMETRIC SENSING AND DISPLAY DEVICE" describes one type of motion sensor that may be used as a motion sensor in an integrated sensor module of the present invention and the entire contents and disclosure of this application is incorporated herein by reference. Such a motion sensor may detect motion by measuring one or more of rectilinear and rotational acceleration, motion or position of the radiation sensor device. In other embodiments, the motion sensor may also measure a change in rectilinear and rotational speed or vector of the radiation sensor device. In one embodiment, the motion sensor may detect motion along at least three degrees of freedom. In other embodiments, the motion sensor may detect motions along six degrees of freedom, etc. The motion sensor may include a single, multiple or combination axis accelerometer to measure the magnitude and direction of acceleration of a motion.

The motion sensor may also include a multi-axis gyroscope that provides orientation information. The multi-axis gyroscope measures rotational rate (d(angle)/dt, [deg/sec]), which may be used to determine if a portion of a body of the user is oriented in a particular direction and/or be used to supplement information from an accelerometer to determine a type of motion performed by the user based on the rotational motion of a user. For example, a walking motion may cause a "pendulum" motion at a wrist of the user, whereas a running motion may cause a cyclic motion at the user wrist along an axis lateral to a direction detected by an accelerometer. Additionally, the motion sensor may use other technologies such as magnetic fields to capture orientation or motion of a user along several degrees of freedom. In one embodiment, the motion sensor sends electrical signals to a processor providing direction and motion data measured by the sensor.

Data about the motion of an individual wearing an integrated sensor module including a motion sensor my processed using a computer or processor that is part of the integrated sensor module and/or by a separate processor or computer that is in wired or wireless communication with the integrated sensor module. The wired or wireless communication may be in real-time. Motion data from the motion sensor may also be transferred from the integrated sensor module to a computer for processing using a storage medium such as a flash memory card or flash memory stick.

In one embodiment, the present invention provides a method and a computer configured to implement a method in which accelerometer displacement measurements (motion activity) is correlated with clock output (time) to determine the period during which an individual was active. This information can in turn be used to determine if a participant was wearing the dosimeter during their designated work period.

In one embodiment, the present invention provides a method and a computer configured to implement a method in which accelerometer displacement measurements (motion activity) is correlated with clock output (time) and with measurements of the on-board sensors (exposure) to determine if the participant was wearing the dosimeter when it was exposed.

In one embodiment, the present invention provides a method and a computer configured to implement a method in which accelerometer displacement measurements (motion activity) are correlated with spatial position (based on data from a GPS or based on data from a position beacon, such as a Bluetooth position beacon) and with exposure to determine if the individual was in an occupationally-monitored work location when the dosimeter was exposed.

In one embodiment, the present invention provides a method and a computer configured to implement a method in which motion activity measured by multiple motion sensors is analyzed to determine where on the body of an individual the individual was wearing a dosimeter when the dosimeter was exposed to radiation.

In one embodiment, the present invention provides a method and a computer configured to implement a method in which motion activity measured by multiple motion sensors to obtain a biometric signature for an individual is analyzed to determine: (1) if the individual wearing the dosimeter was not the person to whom the dosimeter was assigned and (2) the probability that the individual wearing the dosimeter was the person to whom the dosimeter was assigned.

In one embodiment of the invention, the motion data obtained from one or more motion sensors of dosimeter, such an integrated sensor module, may function as a type of biometric data used to identify an individual. The motion sensors may include various types of motion sensors such an accelerometer, a gyroscope, an energy harvest, etc. For example, there may be an existing database containing motion data for the individuals to whom the integrated sensor modules have been assigned. This database may be generated based previous motion data from individuals wearing integrated sensor modules or by using other devices with motion sensors to generate this data for the individuals in the database. By comparing the motion data obtained by the one or more motion sensors of the integrated sensor module to the motion data in the in the database, the computer may: (1) determine the identity of the individual (if identity data for the individual wearing the integrated sensor module is not sent along with the motion data sent to the computer) or confirm the identity of the individual (if identity data for the individual wearing the integrated sensor module is sent along with the motion data sent to the computer) and (2) determine if only a single individual has been wearing the integrated sensor module. In the case of determining the identity of the individual, the motion data from multiple sensors, such as from the accelerometer, from a gyroscope, or from an energy harvester, may be compared to motion data for a plurality of individuals in a database to find a best match. In the case of confirming the identity of an individual, the motion data has identity data for the individual associated with the motion data and the motion data is compared against existing motion data for the individual in the data base.

In one embodiment of the present invention, motion data may be analyzed and used to estimate the probability that the dosimeter was worn by an individual to whom it had been assigned (versus the probability that it was worn by someone other than the participant to whom it had been assigned). Supervised machine learning techniques may be used to train a computer program to classify the data as indicating that a dosimeter has or has not been worn by an individual. Unsupervised machine learning techniques may be used to estimate the probabilities that an individual has worn a dosimeter.

In one embodiment of the present invention, motion data may be generated by motion sensors based upon an individual's motion-activity patterns throughout the course of the work day, such as the individual's walking gait, the individual's breathing pattern, and any characteristic motion-related habits that the individual may have. Previous work has demonstrated the ability to distinguish motion activity for static postures such as standing, sitting, or lying-down, and dynamic postures such as walking, running, climbing stairs, bicycling, and driving in a motorized vehicle. In an example of the present invention, the individual might usually be standing at work, or the individual might stand at a particular time of the day and sit-down at another time of the day. Another example is that an individual might operate machinery that has a characteristic pattern of vibration or motion that can be used to identify deviations from normal use of the dosimeter.

In one embodiment of the present invention a computer may be configured to determine the period(s) of time that an individual has worn the integrated sensor module based on the motion data obtained by the one or more motion sensors of an integrated sensor module and time data from a clock that is on-board the dosimeter or part of a computer being used to analyze the motion data from the motion sensors of the dosimeter.

In one embodiment of the present invention, machine learning algorithms may be used to extract information from the sensor data in order to characterize the motion-activity patterns of individual participants, and in order to correlate motion-activity with other exposure events.

The present invention will now be described by way of the following non-limiting examples.

EXAMPLES

Example 1

U.S. Pat. No. 7,777,396 B2 entitled "IMPACT POWERED DEVICES" issued to Rastegar et al. on Aug. 17, 2010 and herein incorporated by reference describes a sensor device includes an energy harvester for converting mechanical vibrational energy into electrical energy suitable for use in a wireless sensor of the sensor device. Described embodiments include a housing; a powered element disposed on or in the housing; and an impact power producing element housed on or in the housing and operatively connected to the powered element, the impact power producing element producing power upon an impact of at least a portion of the housing with another surface. The energy harvester uses magnet and coil.

Example 2

U.S. Pat. Application Pub. No. 2012/0319404 A1 entitled "BATTERY ASSEMBLY WITH KINETIC ENERGY-BASED RECHARGING" by Joseph et al. published Dec. 20, 2012 and herein incorporated by reference discloses another sensor device includes an energy harvester for converting mechanical vibrational energy into electrical energy suitable for use in a wireless sensor of the sensor device. Described embodiments include a mobile electronic device configured to recharge when oscillated. The electronic device includes a housing with a battery compartment and a battery assembly positioned within the battery compartment. The battery assembly includes a rechargeable storage battery connected to device's battery contacts. The battery assembly includes a charging assembly connected to the rechargeable storage battery, and the charging assembly provides a kinetic energy-based generator operating during the oscillating motion of the electronic device to output electrical current to the rechargeable storage battery. The generator includes: (a) a barrel; (b) a permanent magnet positioned in an elongated chamber of the barrel and sliding within the chamber during movement of the device; and (c) a coil of conductive wire wrapped around an outer surface of the barrel. The chamber, generator magnet, and barrel outer surface receiving the coil all may be non-circular in cross sectional shape or non-cylindrical to improve kinetic energy harvesting. The energy harvester uses magnet and coil design.

Example 3

An example of an alternative type of energy harvester that can be miniaturized and used to power sensors mounted in discrete locations including, for example, on a vehicle or a cargo container includes U.S. Pat. Application Pub. No. 2009/0080138 A1 entitled "FLUIDIC ELECTROSTATIC ENERGY HARVESTER" by Lohndorf et al. published Mar. 26, 2009 and herein incorporated by reference. A variable capacitor is disclosed that operates without moving mechanical parts. In this capacitor electrically conductive electrodes are separated by an enclosed chamber filled with an electrically conductive material. The electrically conductive material can freely vary its position within the chamber. The capacitance of the device will vary as position of the conductive material changes due to external mechanical motion (ex: rotation vibration, etc.) of the device.

Example 4

An example of an energy harvester based upon high-output, organic film-based photovoltaic cells includes EP 2 378 581 B1 entitled "PHOTOVOLTAIC CELL" by Carroll published Jul. 31, 2013 and herein incorporated by reference.

Example 5

A sensor device includes an energy harvester having a thermocouple for converting heat from a human body into electrical energy suitable for use in a wireless sensor of the sensor device. U.S. Pat. Application Pub. No. 2013/0312806 A1 entitled "THERMOELECTRIC APPARATUS AND APPLICATIONS THEREOF" by Carroll published Nov. 28, 2013 and herein incorporated by reference discloses a thermoelectric apparatus and various applications of thermoelectric apparatus. The thermoelectric apparatus comprises at least one p-type layer coupled to at least one n-type layer to provide a pn junction, and an insulating layer at least partially disposed between the p-type layer and the n-type layer, the p-type layer comprising a plurality of carbon nanoparticles and the n-type layer comprising a plurality of n-doped carbon nanoparticles.

Example 5

A sensor device includes an energy harvester for converting radiofrequency energy into electrical energy suitable for use in a wireless sensor of the sensor device. The energy harvester has radiofrequency receiver coils that are integrated in the fabric of a piece of clothing in order to maximize energy collection and sensing capabilities (See information provided at http://www.wfu.edu/nanotech/News.html which is incorporated herein incorporated by reference.

Example 6

A sensor device includes an energy harvester for converting light generated by any source including sunlight (solar energy), artificial lighting or laser beam into electrical energy suitable for use in a wireless sensor of the sensor device.

Example 7

Additional examples of mechanical energy harvesters include:

U.S. Pat. No. 8,704,387 B2 entitled "ELECTRICAL ENERGY GENERATOR" issued to Lemieux on Apr. 22, 2014 and herein incorporated by reference describes an electrical energy generator comprising a housing having a longitudinal axis and opposite ends, an electromagnetically active mass positioned within the housing reciprocally movable along at least a portion of the longitudinal axis, an electrically conductive material within the housing, a body engaged with the electromagnetically active mass, and at least one spring positioned between at least one of an end of the housing and an end of the body, or between an end of the body and the electrically conductive material.

U.S. Pat. No. 8,674,526 B2 entitled "ELECTRICAL ENERGY GENERATOR" issued to Lemieux on Mar. 18, 2014 and herein incorporated by reference describes an electrical energy generator including a housing, an electromagnetically active mass positioned within the housing, an electrically conductive material within the housing, a body positioned within the housing wherein the body and the electromagnetically active mass move relative to each other, and at least one spring for imparting restorative forces to the electromagnetically active mass and the body.

Thus, disclosed embodiments relate generally to a power source for sensors. More specifically, the invention relates to an energy harvester that converts mechanical vibration, light, heat (e.g., heat from a body, a combustion device, or other heat-generating thermocouples), radiofrequency, or other forms of energy into electrical energy suitable for use in small, wireless autonomous devices, for example, portable sensors, wearable electronics, motion sensors, wireless sensor networks, sensor-enabled fabrics and other wearable, portable or mobile products.

Example 8

An example of using accelerometer sensor data to obtain information that can be used to characterize the activity of individuals based upon characteristic motion patterns (activity recognition) is described in Ravi N, Dandekar N, Mysore P, Littman M L, "Activity Recognition from Accelerometer Data," American Association for Artificial Intelligence, 2005 (hereinafter "Ravi et al." FIG. 3 of Ravi et al. shows a graph of accelerometer data classified by activity).

Example 9

An example of using multiple sensors, including accelerometer, audio microphone, and video camera to obtain different types of information that can be used to characterize the activity of individuals is described in Casale P, Pujol O, Radeva P, "Human Activity Recognition from Accelerometer Data Using a Wearable Device," LNCS, 6669, 289-296, 2011 (hereinafter "Casale et al.") Casale, et al. incorporate a microphone and video camera (with audio and video post-processing) to help characterize motion activities.

Example 10

An example of using accelerometer sensor data to obtain biometric information that can be used to identify individuals based upon characteristic walking patterns (biometric gait) is described in Gafurov D, Helkala K, Sondrol T, "Biometric Gait Authentication Using Accelerometer Sensor," Journal of Computers, 1(7):51-59, 2006 (hereinafter "Gafurov et al."). Gafurov et al. demonstrates the ability to distinguish between different individuals by performing a histogram similarity metric and a cycle length metric to accelerometer displacement data acquired from a three-axis accelerometer positioned on the participant's leg.

Example 11

Mannini A, Sabatini A M, "Machine Learning Methods for Classifying Human Physical Activity from On-body Accelerometers," Sensors, 10:154-1175, 2010 provides a review of the machine-learning methods that have been developed to classify human motion activity, please see the following reference:

Example 12

An example of using accelerometer sensor data to obtain motion information that can be used to identify the mode of transportation by which an individual is moving is described in Bedogni L, Di Felice M. Bononi L, "By Train or By Car? Detecting the User's Motion Type through Smartphone Sensors Data," IEEE, 2012 (hereinafter "Bedogni et al.") Bedogni et al. demonstrates the ability to use the accelerometer data in a smartphone to determine if the individual was walking, driving in a car, or riding in a train. This approach could be used to characterize the motion of other types of motorized vehicles. In one embodiment, the present invention may be used to monitor non-living entities such as transport vehicles and cargo containers to identify and prevent the potentially illegal transportation or storage of hazardous substances.

Example 13

Figure 12:
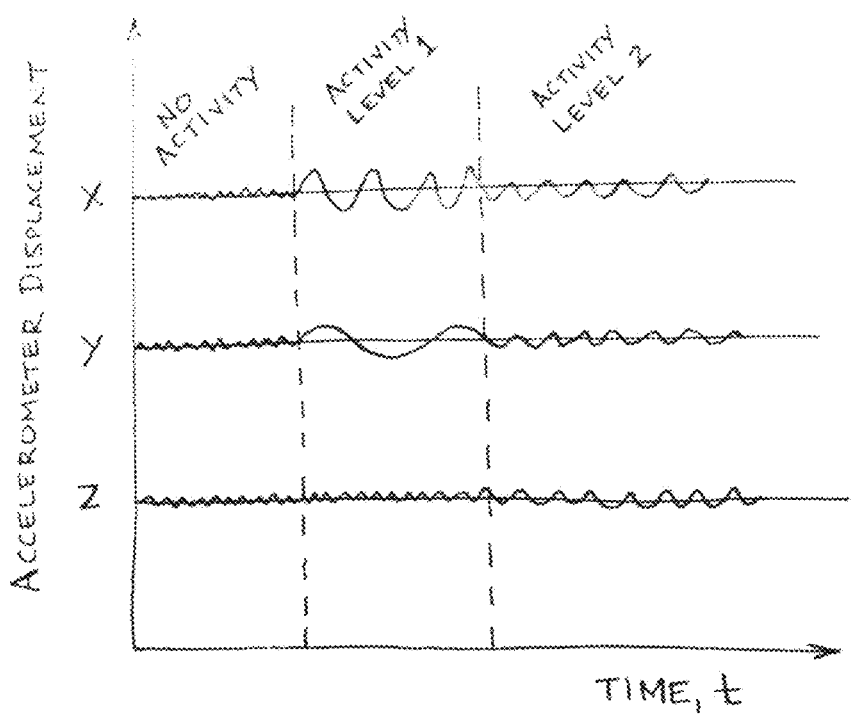
FIG. 12 is an illustrative graph of motion data from an accelerometer for a dosimeter worn by an individual.

FIG. 12 shows an exemplary graph of accelerometer displacement in the x-axis of direction, the y-axis of direction and the z-axis of direction vs. time of an accelerometer that is one of the motion sensors of a dosimeter. When a person is not active or the dosimeter is not worn by the individual, there is no or minimal displacement in the x-axis of direction, the y-axis of direction and the z-axis of direction as shown in the period of time labeled "No Activity". During the time period labeled "Activity Level 1" there are frequent changes in the direction of motion of the accelerometer along x-axis of direction, less frequent changes in direction of motion along the z-axis of direction and virtually no change in motion along the z-axis of direction. In the time period labeled "Activity Level 2" there are moderate amounts of changes in the direction of motion along the x-axis of direction, the y-axis of direction and the z-axis of direction.

Example 14

Figure 13:
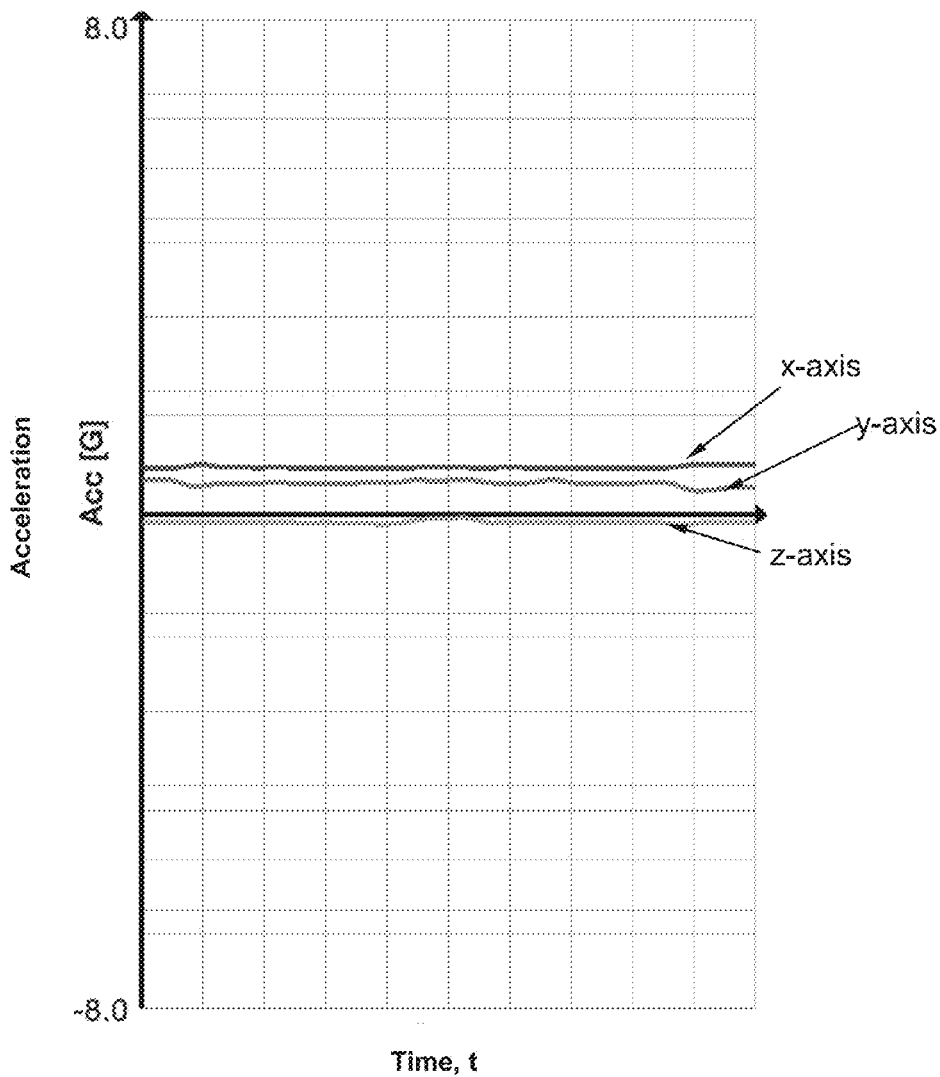
FIG. 13 is an illustrative graph of motion data from an accelerometer for a dosimeter worn by an individual while the individual is sitting with minimal or no motion.
Figure 14:
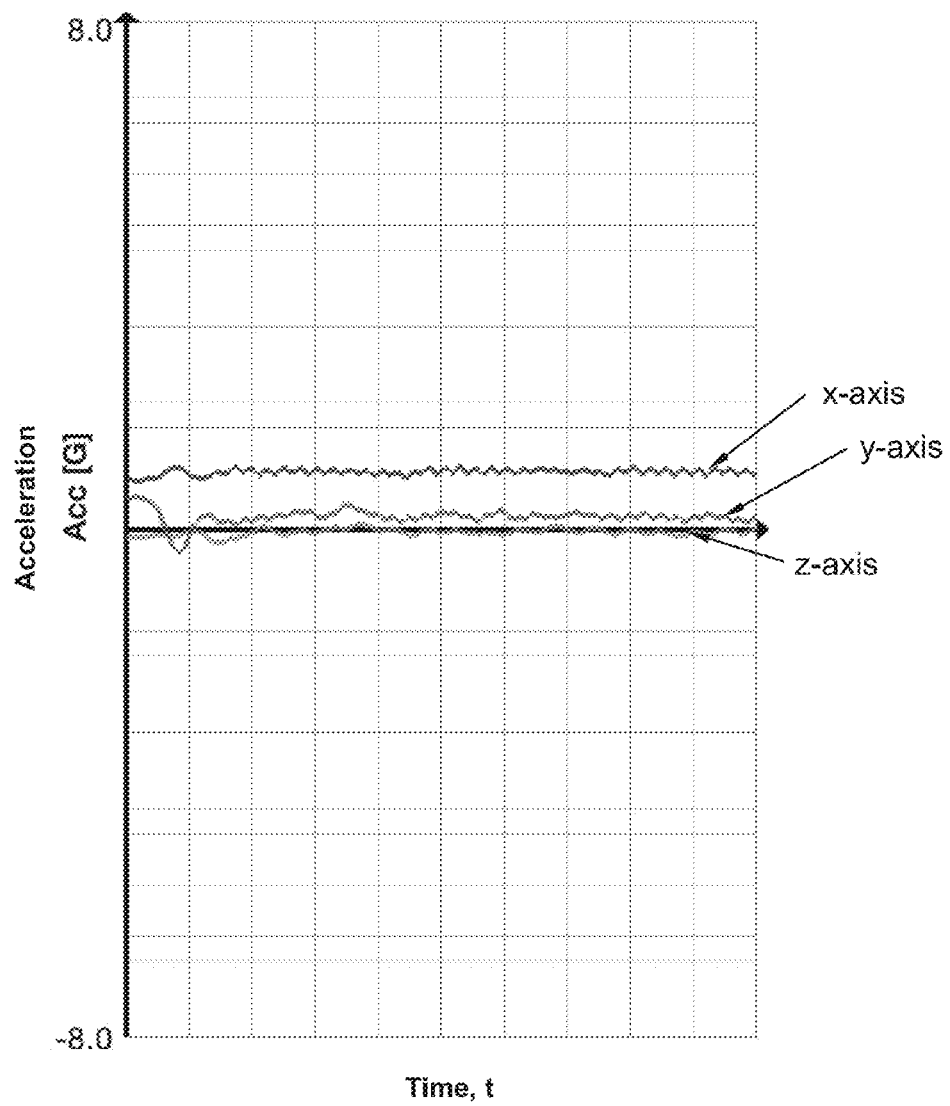
FIG. 14 is an illustrative graph of motion data from an accelerometer for a dosimeter worn by an individual while the individual walking.
Figure 15:
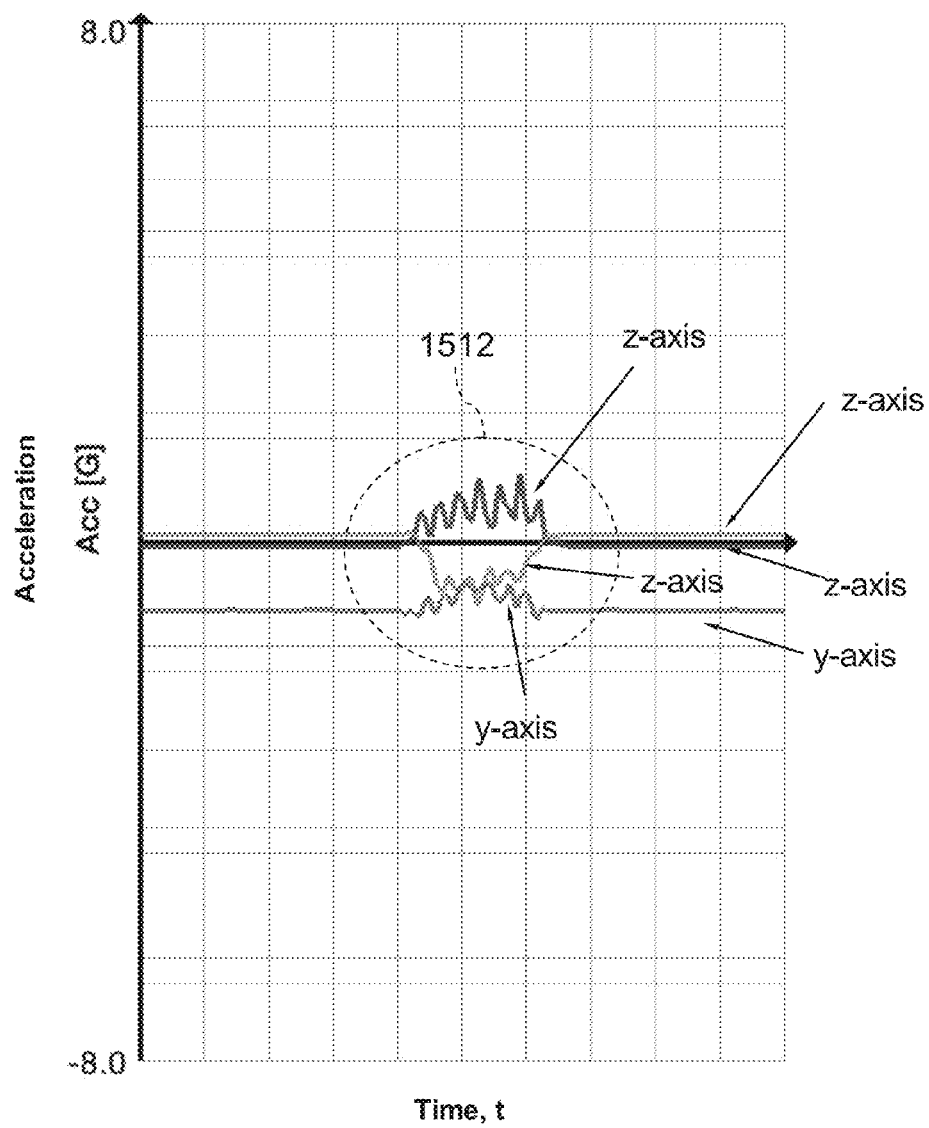
FIG. 15 is an illustrative graph of motion data from an accelerometer for dosimeter worn by an individual who is standing still, then waving the individual's arms, then standing still.

FIGS. 13, 14 and 15 shows exemplary graphs of accelerometer displacement (acceleration) in the x-axis of direction, the y-axis of direction and the z-axis of direction vs. time of an accelerometer that is one of the motion sensors of a dosimeter. FIG. 13 shows the displacement of the accelerometer when an individual wearing a dosimeter is sitting with minimal or no motion. In FIG. 13 there is no or minimal displacement in the x-axis of direction, the y-axis of direction and the z-axis of direction. FIG. 14 shows the displacement of the accelerometer when an individual wearing a dosimeter is walking. In FIG. 14, small amounts of motion occur along all three axes of direction as shown by the frequent small amplitude changes in displacement. FIG. 15 shows the displacement of the accelerometer when an individual wearing a dosimeter stands without moving followed by the individual moving the individual's arms and then followed by the individual standing again. During the period of the individual moving the individual's arms, indicated by dashed oval 1512 in FIG. 15, significant amounts of motion occur along all three axes of direction as shown by the frequent small amplitude changes in displacement.

The devices and subsystems of the disclosed exemplary embodiments can store information relating to various processes described herein. This information can be stored in one or more memories, such as a hard disk, optical disk, magneto-optical disk, RAM, and the like, of the devices and subsystems of the disclosed exemplary embodiments. One or more databases of the devices and subsystems of the disclosed exemplary embodiments can store the information used to implement the exemplary embodiments of the present invention. The databases can be organized using data structures (e.g., records, tables, arrays, fields, graphs, trees, lists, and the like) included in one or more memories or storage devices listed herein. The processes described with respect to the disclosed exemplary embodiments can include appropriate data structures for storing data collected and/or generated by the processes of the devices and subsystems of the disclosed exemplary embodiments in one or more databases thereof.

All or a portion of the devices and subsystems of the disclosed exemplary embodiments can be conveniently implemented using one or more general purpose computer systems, microprocessors, digital signal processors, microcontrollers, and the like, programmed according to the teachings of the exemplary embodiments of the present invention, as will be appreciated by those skilled in the computer and software arts. Appropriate software can be readily prepared by programmers of ordinary skill based on the teachings of the exemplary embodiments, as will be appreciated by those skilled in the software art. In addition, the devices and subsystems of the disclosed exemplary embodiments can be implemented by the preparation of application-specific integrated circuits or by interconnecting an appropriate network of conventional component circuits, as will be appreciated by those skilled in the electrical art(s). Thus, the exemplary embodiments are not limited to any specific combination of hardware circuitry and/or software.

Stored on any one or on a combination of computer readable media, the exemplary embodiments of the present invention can include software for controlling the devices and subsystems of the disclosed exemplary embodiments, for driving the devices and subsystems of the disclosed exemplary embodiments, for enabling the devices and subsystems of the disclosed exemplary embodiments to interact with a human user, and the like. Such software can include, but is not limited to, device drivers, firmware, operating systems, development tools, applications software, and the like. Such computer readable media further can include the computer program product of an embodiment of the present invention for performing all or a portion (if processing is distributed) of the processing performed in implementing the disclosed exemplary embodiments. Computer code devices of the exemplary embodiments of the present invention can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the exemplary embodiments of the present invention can be distributed for better performance, reliability, cost, and the like.

As stated above, the devices and subsystems of the disclosed exemplary embodiments can include computer readable medium or memories for holding instructions programmed according to the teachings of the present invention and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave, or any other suitable medium from which a computer can read.

While the present invention has been disclosed with references to certain embodiments, numerous modifications, alterations, and changes to the described embodiments are possible without departing from the spirit and scope of the present invention, as defined in the appended claims. Accordingly, it is intended that the present invention not be limited to the described embodiments, but that it has the full scope defined by the language of the following claims, and equivalents thereof.

REFERENCES

1. S. R. Anton, H. A. Sodano, A review of power harvesting using piezo-electric materials (2003-2006), Smart Mater. and Struct. 16 (3) (2007) R1-R21. doi: 10.1088/0964-1726/16/3/R01.
2. S. P. Beeby, M. J. Tudor, N. M. White. Energy harvesting vibration sources for microsystems applications, Meas. Sci. and Tech. 17 (12) (2006) R175-R195. doi:10.1088/0957-0233/17/12/R01.
3. P. Mitcheson, E. Yeatman, G. Rao, A. Holmes, T. Green, Energy Harvesting From Human and Machine Motion for Wireless Electronic Devices. Proceedings of the IEEE 96 (9) (2008) 1457-1486. doi:10.1109/JPROC.2008.927494.
4. S. Roundy, P. K. Wright, A piezoelectric vibration based generator for wireless electronics, Smart Mater. and Struct. 13 (5) (2004) 1131-1142.
5. A. Erturk, D. J. Inman, An experimentally validated bimorph cantilever model for piezoelectric energy harvesting from base excitations, Smart Materials and Structures 18 (2) (2009) 025009.
6. D. F. Berdy, P. Srisungsitthisunti, B. Jung, X. Xu, J. F. Rhoads, D. Peroulis, Low-frequency meandering piezo-electric vibration energy harvester. IEEE transactions on ultrasonics, ferroelectrics, and frequency control 59 (5) (2012) 846-58. doi:10.1109/TUFFC.2012.2269.
7. C. Williams, R. Yates, Analysis of a micro-electric generator for microsystems, Proceedings of the International Solid-State Sensors and Actuators Conference—TRANSDUCERS '95 44 (0) (1995) 369-372. doi:10.1109/SENSOR.1995.717207.
8. S. P. Beeby. R. N. Torah, M. J. Tudor, P. Glynne-Jones, T. O'Donnell, C. R. Saha, S. Roy, A micro-electromagnetic generator for vibration energy harvesting, J. Micromech. Microeng. 17 (7) (2007) 1257-1265.
9. S. Roundy, P. Wright, J. Rabaey, A study of low level vibrations as a power source for wireless sensor nodes. Computer Communications 26 (2003) 1131-1144.
10. S. Meninger, J. Mur-Miranda, R. Amirtharajah, A. Chandrakasan, J. Lang, Vibration-to-electric energy conversion, IEEE Transactions on Very Large Scale Integration (VLSI) Systems 9 (1) (2001) 64-76.
11. L. Wang, F. G. Yuan, Vibration energy harvesting by magnetostrictive material, Smart Materials and Structures 17 (4) (2008) 045009.
12. E. K. Reilly, L. M. Miller, R. Fain, P. K. Wright, A study of ambient vibrations for piezoelectric energy conversion, in: Proc. PowerMEMS, Washington D.C., 2009, pp. 312-315.
13. S. Lam Po Tang, Recent developments in flexible wearable electronics for monitoring applications, Transactions of the Institute of Measurement and Control 29 (3-4) (2007) 283-300. doi:10.1177/0142331207070389.
14. B. Lo, S. Thiemjarus, R. King, G. Yang, Body sensor network: a wireless sensor platform for pervasive healthcare monitoring, Conference on Pervasive Computing Technologies for Healthcare (2005) 77-80.
15. K. Sun, G. Q. Liu, X. Y. Xu, Nonlinear Resonant Generator for Harvesting Energy from Human Wrist Vertical Shaking, Applied Mechanics and Materials 128-129 (2011) 923-927. doi:10.4028/www.scientific.net/AMM.128-129.923.
16. C. Saha, T. ODonnell, N. Wang, P. McCloskey, Electromagnetic generator for harvesting energy from human motion, Sensors and Actuators A: Physical 147 (1) (2008) 248-253. doi: 10.1016/j.sna.2008.03.008.
17. P. Constantinou, P. H. Mellor, P. D. Wilcox, A Magnetically Sprung Generator for Energy Harvesting Applications. IEEE/ASME Transactions on Mechatronics 17 (3) (2012) 415-424. doi:10.1109/TMECH.2012.2188834.
18. X. Yang, B. Zhang, J. Li, Y. Wang, Model and Experimental Research on an Electromagnetic Vibration-Powered Generator With Annular Permanent Magnet Spring, IEEE Transactions on Applied Superconductivity 22 (3) (2012) 5201504-5201504. doi:10.1109/TASC.2011.2179401.
19. A. R. M. Foisal, B.-C. Lee, G.-S. Chung, Fabrication and performance optimization of an AA size electromagnetic energy harvester using magnetic spring, 2011 IEEE SENSORS Proceedings (2011) 1125-1128doi:10.1109/ICSENS.2011.6126947.
20. P. Constantinou, P. Mellor, P. Wilcox, A Model of a Magnetically Sprung Vibration Generator for Power Harvesting Applications, in: 2007 IEEE International Electric Machines & Drives Conference, IEEE, 2007, pp. 725-730. doi:10.1109/IEMDC.2007.382757.
21. E. Dallago, M. Marchesi, G. Venchi. Analytical Model of a Vibrating Electromagnetic Harvester Considering Nonlinear Effects, IEEE Transactions on Power Electronics 25 (8) (2010) 1989-1997. doi:10.1109/TPEL.2010.2044893.
22. B. Mann, N. Sims. Energy harvesting from the nonlinear oscillations of magnetic levitation, Journal of Sound and Vibration 319 (1-2) (2009) 515-530. doi: 10.1016/j.jsv.2008.06.011.
23. A. R. M. Foisal, C. Hong, G.-S. Chung, Multi-frequency electromagnetic energy harvester using a magnetic spring cantilever, Sensors and Actuators A: Physical 182 (2012) 106-113. doi:10.1016/j.sna.2012.05.009.
24. G. P. Beyer, G. G. Mann, J. A. Pursley, E. T. Espenhahn, C. Fraisse, D. J. Godfrey, M. Oldham, T. B. Carrea, N. Bolick, and C. W. Scarantino, "An implantable MOSFET dosimeter for the measurement of radiation dose in tissue during cancer therapy," IEEE Sensors Journal, vol. 8, 2008.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

What is claimed is:
1. A method comprising the following steps:
 (a) determining a first period of time that an individual has been active based on motion data for a dosimeter worn by the individual and time data associated with the motion data, and
 (b) reporting the first period of time the individual has been active via a visual display device and/or via saving the first period of time the individual has been active to a storage medium,
 wherein the dosimeter comprises one or more motion sensors for generating the motion data.
2. The method of claim 1, wherein step (a) comprises comparing accelerometer displacements measurements from the dosimeter to the time data to thereby determine the first period of time.
3. The method of claim 1, wherein the method comprises the following step:

(c) determining a second period of time that dosimeter has been worn by the individual based on motion data for the dosimeter.

\* \* \* \* \*